United States Patent
Missalla et al.

(10) Patent No.: US 12,203,033 B2
(45) Date of Patent: Jan. 21, 2025

(54) HIGH EFFICIENCY PROCESS FOR SEPARATING FILLERS FROM CATALYST AND GASES IN A FLUID BED CATALYTIC PYROLYSIS PROCESS

(71) Applicant: Anellotech, Inc., Pearl River, NY (US)

(72) Inventors: Michael Missalla, Oberursel (DE); Leslaw Mleczko, Dormagen (DE); Karl-Ernst Wirth, Erlangen (DE); Omar M. Basha, Wilmington, DE (US)

(73) Assignee: Anellotech, Inc., Pearl River, NY (US)

( * ) Notice: Subject to any disclaimer, the term of this patent is extended or adjusted under 35 U.S.C. 154(b) by 0 days.

(21) Appl. No.: 18/143,044

(22) Filed: May 3, 2023

(65) Prior Publication Data

US 2023/0357106 A1    Nov. 9, 2023

Related U.S. Application Data

(60) Provisional application No. 63/338,013, filed on May 3, 2022.

(51) Int. Cl.

| | |
|---|---|
| *C10G 1/10* | (2006.01) |
| *B01J 8/00* | (2006.01) |
| *B01J 8/18* | (2006.01) |
| *C07C 4/06* | (2006.01) |
| *C10B 53/07* | (2006.01) |
| *C10B 57/02* | (2006.01) |
| *C10B 57/06* | (2006.01) |
| *C10G 47/30* | (2006.01) |

(52) U.S. Cl.
CPC .............. *C10G 1/10* (2013.01); *B01J 8/0055* (2013.01); *B01J 8/1818* (2013.01); *C07C 4/06* (2013.01); *C10B 53/07* (2013.01); *C10B 57/02* (2013.01); *C10B 57/06* (2013.01); *C10G 47/30* (2013.01); *C07C 2529/40* (2013.01); *C10G 2300/1003* (2013.01); *C10G 2300/4006* (2013.01); *C10G 2300/4012* (2013.01); *C10G 2400/20* (2013.01); *C10G 2400/30* (2013.01)

(58) Field of Classification Search
None
See application file for complete search history.

(56) References Cited

U.S. PATENT DOCUMENTS

| | | | |
|---|---|---|---|
| 4,010,094 A * | 3/1977 | McKinney | ................. B01J 8/26 502/42 |
| 4,029,716 A | 6/1977 | Kaeding | |
| 9,803,035 B2 | 10/2017 | Layman et al. | |
| 10,465,058 B2 | 11/2019 | Layman et al. | |
| 11,008,433 B2 | 5/2021 | Layman et al. | |
| 2002/0033098 A1* | 3/2002 | Hiltunen | ................... B04C 5/28 95/269 |

(Continued)

OTHER PUBLICATIONS

MAAG "High quality polymer filtration", Accessed Jul. 29, 2023.

(Continued)

*Primary Examiner* — In Suk C Bullock
*Assistant Examiner* — Alyssa L Cepluch
(74) *Attorney, Agent, or Firm* — Frank Rosenberg

(57) ABSTRACT

A process that separates the fillers found in plastics from catalyst and the gases in a fluid bed catalytic pyrolysis process for the conversion of waste plastics, polymers, and other waste materials to useful chemical and fuel products such as paraffins, olefins, and aromatics such as BTX, is described.

18 Claims, 9 Drawing Sheets

(56) References Cited

U.S. PATENT DOCUMENTS

| | | | | |
|---|---|---|---|---|
| 2008/0230444 A1* | 9/2008 | Iwadate | .................. | C10J 3/482 |
| | | | | 422/198 |
| 2012/0215043 A1* | 8/2012 | Gaffney | .................. | B01J 29/90 |
| | | | | 502/64 |
| 2016/0129413 A1* | 5/2016 | Kulprathipanja | ...... | C10G 11/18 |
| | | | | 422/234 |
| 2018/0057753 A1* | 3/2018 | Heiskanen | .............. | C10B 57/18 |
| 2020/0362248 A1* | 11/2020 | Cartolano | ............ | C10G 11/182 |
| 2022/0010213 A1* | 1/2022 | Sun | ......................... | C10B 57/06 |

OTHER PUBLICATIONS

Muschelknautz, Edgar, and Volker Greif. "Cyclones and other gas—solids separators."Beds, (1997) 181-213.

Hugi, Erich, and Lothar Reh. "Focus on solids strand formation improves separation performance of highly loaded circulating fluidized bed recycle cyclones." Chemical Engineering and Processing: Process Intensification 39 (3) (2000) 263-273.

Huber, G.W. et al., "Synthesis of Transportation Fuels from Biomass: Chemistry, Catalysts, and Engineering," Chem. Rev. 106, (2006), pp. 4044-4098.

Klumpar, V. I., "Measuring and Optimizing Air Classifier Performance," Sep. Technol., 2 (3), 1992, 124-135.

\* cited by examiner (a) With cone

HIGH EFFICIENCY PROCESS FOR SEPARATING FILLERS FROM CATALYST AND GASES IN A FLUID BED CATALYTIC PYROLYSIS PROCESS

RELATED APPLICATIONS

This claims the priority benefit of U.S. Provisional Patent Application Ser. No. 63/338,013 filed 3 May 2022.

FIELD OF THE INVENTION

This invention relates to the conversion of waste plastics, polymers, and other waste materials to useful chemical and fuel products such as paraffins, olefins, and aromatics such as BTX in a process that includes a high efficiency process for separating fillers from the catalyst particles used in the upgrading of such waste materials.

INTRODUCTION

In 2019, plastics generation in the United States was 55.2 million tons, which was 13 percent of MSW generation. World-wide over 368 million tons of plastics were produced. By some estimates, of the 8.3 billion tons of plastics ever produced, 6.3 billion tons ended up as waste, of which only 9% has been recycled. Plastic recycling recovers scrap or waste plastic and reprocesses the material into useful products. However, since China banned the import of waste plastics in 2018 the recycle rate in the US is estimated to have dropped to only 4.4%. Plastic recycling is challenging due to the chemical nature of the long chain organic polymers and low economic returns. Waste plastic materials often need sorting into the various plastic resin types, e.g. low density polyethylene (LDPE), high density polyethylene (HDPE), polypropylene (PP), polystyrene (PS), polyvinyl chloride (PVC), and polyethylene-terephthalate (PET) for separate recycling treatments. In addition, plastic materials often contain particulate materials introduced into a polymer formulation to reduce the costs and improve the properties. The materials added to plastics formulations, so-called fillers, occupy space and replace the expensive resin with less expensive compounds. Cost reduction depends on the relative cost of the polymer and the filler. Polymer price ranges in May 2020 were approximately ($/kg): ABS 10-16.5, HDPE 3.8-8.6, PET 1-3, PP 2.3-3.7, PS 10.9-16.8, and PVC 1.8-2.5, whereas fillers are generally much less than $1/kg. The global plastic filler market was estimated at US$10 billion in 2019 and is expected to surpass US$14.5 billion by 2026 with a growth rate of 5.2%. Many of these fillers make the plastics easier to mold and shape while ensuring their stability. For plastics that require heat-resistance, mineral fillers can increase heat-deflection and reduce thermal expansion. Larger size filler particles provide a site for cracks to grow, weakening the material. Particles larger than about 10-20 microns start to seriously affect the impact resistance and elongation to break of a composite. Coarser particles also lead to poor surface finish, i.e. low gloss, and increased permeability. Thus, fillers are generally preferred to be very small particles, less than about 30 microns.

When fillers are included in a polymer they typically account for 20-30% of the mass of the composite. However, some materials, such as PVC, are produced that contain as much as 90 mass % filler, and other materials contain less than 0.1% filler by weight.

Plas-TCat™ is a catalytic fluid bed process using zeolite catalysts to convert polymer/plastic material, especially waste plastics that otherwise might be sent to a landfill or incinerator, to a mixed product of permanent gases, C2-C4 light olefins, C1-C4 light paraffins, and C5+ hydrocarbons including benzene, toluene, and xylenes ("BTX"), aromatic and non-aromatic naphtha range molecules, C11+ hydrocarbons, coke and char, and minor byproducts. Plastic mixtures that have relatively high hydrogen to carbon molar ratio, such as polyethylene (PE), polypropylene, polystyrene, and combinations thereof, can be converted to olefins and aromatics. In Plas-TCat™ materials such as fillers, inorganics, salts, minerals, orbits of glass or metal must be continuously removed from the process to avoid accumulation, which can both decrease catalyst activity and adversely affect reactor hydrodynamics.

In the Plas-TCat™ process, fillers will be elutriated in the gaseous effluent of both the reactor and regenerator, in addition to some entrained catalyst, resulting in a bimodal distribution of solids in the gaseous effluent stream, i.e. smaller particles of fillers (<40 microns, 95%<20 microns) and larger particles of catalyst (>40 microns, 95%>65 microns). Effective separation of the fillers from this stream, while minimizing catalyst losses from the process, is critical to stabilize performance and minimize catalyst costs.

Removal of fillers from plastics by filtration of a hot melt can be carried out by use of screen or candle filters, such as those offered by MAAG (https://maag.com/wp-content/uploads/LAF%20Brosch%C3%BCre_EN_16S_s.pdf). Filtration of hot melts of plastics requires raising the mixture to high temperatures (to 400° C.) and high pressure (to 300 bar) to force the viscous molten plastic through the filters, and regular cleaning or replacement of the filter elements that requires taking the process off-line.

Dissolution plastics recycling involves dissolving the polymer in a solvent for separation of solids, as practiced in the CreaSolv® Technology (https://www.creacycle.de/en/) applied to polystyrene or PureCycle technology for polypropylene. The process requires filtration of the polymer solution to remove particulate matter. In addition to the problems that arise from regular cleaning or replacement of the filters, the process requires large volumes of costly solvent and nearly 100% recovery of the solvent to be viable. The process is further limited to polymers of one type or polymer mixtures in which all of the polymers in the mixture dissolve in the same solvent, that requires additional separation of the mixtures of polymers found in real-world recycle streams into individual component polymers.

Layman et al in U.S. Pat. No. 9,803,035 describe a process for purifying polyethylene by contacting it at elevated temperature and pressure with a fluid solvent and contacting the polyethylene solution with solid media to produce a purer polyethylene solution. Layman et al in U.S. Ser. No. 10/465,058 describe a process for purifying reclaimed polymer by dissolving a polymer in solvent, settling the solution to remove suspended contaminants, purifying the solution by contact with solid media, and separating the polymer from the resulting solution. Layman et al in U.S. Ser. No. 11/008,433B2 describe a process for purifying reclaimed polymer by dissolving a polymer in solvent, settling the solution to remove suspended contaminants, purifying the solution by contact with solid media, and separating the polymer from the resulting solution, and repeating the process for different polymers in the mixture.

All of the dissolution processes require handling of large quantities of solvent and constitute a separate process from a polymer chemical recycling process.

There is a need for a simple, continuous process for chemically recycling mixtures of polymers that contain fillers to chemical intermediates for further upgrading.

SUMMARY OF THE INVENTION

The present invention provides a simple system and continuous, one step method for separating solids from a continuous reactor effluent gas stream resulting from the pyrolysis of a carbonaceous feed containing a high concentration (up to 10%) of fillers. The configuration comprises a multi-stage cyclone system, the first stage preferably being a single cyclone, with the second and later stages each comprising axial-type multi-cyclones (multiclones) operating in parallel. The efficiency of the first cyclone is adjusted to a level to allow as much as possible of the fillers (smaller particles) to exit with the cyclone gas and as much as possible of the catalyst (larger particles) to exit from the bottom of the cyclone. For the present invention, the target is for at least 85% of the fillers (smaller diameter component) in the inlet gas stream to exit along with the cyclone gas (top) exit, and to separate at least 95% of the catalyst (larger diameter component) from the inlet gas stream that passes out of the bottom of the cyclone and return it to the reactor. The dimensions of the cyclone are adjusted with the minimum objective of meeting these separation targets and to exceed them to the maximum achievable value. Subsequent stages operate at efficiencies to further reduce the amount of filler in the effluent gas leaving the reactor to meet solids loading restrictions into downstream processing units.

I. Klumpar et. al., in "Air Classifiers", *Chemical Engineering*, March 1986, show different classifiers and their size selectivity curves. In general, it can be said that they do not reach the present cut size and they have lower efficiency. This effect of industrial classifiers is described as sharpness index which leads to bypasses of up to 30%! Other sources, such as Metso Air Classifier (https://www.mogroup.com/products-and-services/plants-and-capital-equipment/classifiers/air-classifiers/), claim cut sizes down to 10 μm with limitations to top size particle size of 500 μm. Any of several routine scientific methods may be used to determine the particle size distribution (PSD) of a mixture, such as light scattering, X-ray diffraction (XRD), scanning electron microscopy (SEM), transmission electron microscopy (TEM), and scanning transmission electron microscopy (STEM).

Without wishing to be bound by theory, the present method uses the strand separation effect in highly loaded cyclones and the bimodal particle size distribution of the entering solids stream. Generally, the separation behavior (or efficiency) of a highly loaded cyclone consists of two main mechanisms: (1) The restricted turbulence in the cyclones allows for only certain loadings of solids to be carried with the inlet gas stream, also referred to as the critical load. If the solids loading in the gas exceeds this critical loading value, the excess solids mass is removed immediately after the cyclone inlet and forms strands or a continuous layer at the wall (strand separation). (2) Only a small fraction of the finer particle size distribution remains in the gas flow and undergoes centrifugal separation in the vortex of the cyclone (Inner separation). Inner separation is governed by the balance between centrifugal forces and particle drag.

Strand separation becomes the more dominant mechanism at solid loadings greater than around 0.05 kg/kg as shown in Muschelknautz, Edgar, and Volker Greif. "Cyclones and other gas-solids separators." *Circulating Fluidized Beds*. Springer, Dordrecht, 1997. 181-213, and in Hugi, Erich, and Lothar Reh. "Focus on solids strand formation improves separation performance of highly loaded circulating fluidized bed recycle cyclones." *Chemical Engineering and Processing: Process Intensification* 39.3 (2000): 263-273.

Both of these separation mechanisms are characterized by a cut size, which is a function of the gas and solid physical properties and the cyclone geometry, and describes the particle size boundary between the larger solids undergoing strand separation and the smaller solids undergoing inner separation. Cyclones are typically designed such that the cut size is as small as possible, resulting in maximum removal of solids from the gas stream and thus maximizing separation efficiency. In this proposed application, the cyclone is designed such that only the catalyst (larger) particles will undergo strand separation and be readily removed from the gas stream, while the rest of the solids (fillers) will remain in the gas flow in the vortex of the cyclone, which is designed to reduce solids loss due to inner separation, specifically by modifying the dimensions of the vortex finder. These smaller solids (fines) subsequently exit the cyclone with the gas stream. Effectively operating the cyclone as a solids classifier.

The first cyclone is designed to have its cut size between the bimodal particle size distribution allowing the coarse fraction to be separated and the fine fraction being entrained in the off-gas for removal in one or a series of high efficiency multiclones. The high efficiency multiclones are used to reduce the concentration of elutriated particles to meet solids loading restrictions for the downstream process.

The present invention provides a method of producing olefinic and aromatic hydrocarbons from waste plastics comprising feeding a stream comprising plastics to a fluid bed catalytic pyrolysis reactor, catalytically reacting the feed with the catalyst to form a product mixture, passing the vapor effluent through a catalyst and filler recovery system comprising classifier cyclones and recovery cyclones, returning solids from the classifier cyclones to the fluidized bed reactor, discarding fillers recovered from the recovery cyclones, and recovering olefins, or aromatics from the vapor exiting the last recovery cyclone.

A first aspect of this invention provides a method of converting plastics to olefins, or aromatics, or a mixture of olefins and aromatics, comprising: feeding a stream comprising plastics at least one of which contains filler material to a fluid bed reactor containing a catalyst; wherein the filler material has an average particle size that is smaller than the average particle size of the fluid bed catalyst; catalytically reacting the feed with the catalyst in the fluidized bed reactor to form a product mixture; recovering a vapor effluent from the product mixture; passing the vapor effluent through a solids separation system; separating catalyst from filler materials, and recovering olefins, or aromatics, or some combination thereof from the vapor exiting the last recovery cyclone.

A second aspect of this invention provides a method for producing olefins and aromatics comprising: feeding a stream comprising plastics at least one of which contains filler material to a fluidized bed reactor comprising a catalyst; wherein the filler material has a cut size or particle size that is smaller than the cut size or particle size of the fluid bed catalyst; catalytically reacting the feed with the catalyst in the fluidized bed reactor to form a product mixture comprising a first mass ratio of catalyst to filler material; recovering a vapor effluent from the product mixture, wherein the vapor effluent comprises catalyst particles and filler material; passing the vapor effluent through a solids separation system comprising passing the vapor effluent into a first cyclone and separating a first bottoms fraction and a first overflow fraction; wherein the first cyclone is a classifier cyclone; wherein the first bottoms fraction has a second mass ratio that is greater than the first mass ratio; passing the overflow fraction into a second cyclone and separating a second bottoms fraction and a second overflow fraction; wherein the first cyclone has a first separation efficiency for the catalyst particles and the second cyclone has a second separation efficiency for the catalyst particles that is greater than the first separation efficiency; wherein the second bottoms fraction has a third mass ratio that is less than the first mass ratio; and recovering olefins, or aromatics, or some combination thereof from the second overflow fraction vapor exiting the last cyclone.

The second overflow fraction may pass through additional cyclones prior to the step of recovering. Particle size in the claimed method can be measured by X-ray diffraction (XRD), scanning electron microscopy (SEM), transmission electron microscopy (TEM), or scanning transmission electron microscopy (STEM). Size can be quantified as the median diameter for volume fraction smaller than 50 vol % according to ASTM D4464-00.

The invention, in other aspects, includes any of the apparatus, systems (apparatus plus conditions and/or chemical streams), or methods described herein.

In any of its aspects, the invention may be further characterized by one or any combination of the following features: wherein the solids separation system comprises one or more low efficiency or classifier cyclones or one or more recovery cyclones or multiclones, or both; wherein the flow velocity at the entrance to the low efficiency or classifier cyclone is greater than the flow velocity at the entrance to the recovery cyclones; wherein at least a portion of the solids recovered in the bottoms from the one or more low efficiency or classifier cyclones is returned to the fluidized bed reactor; wherein at least a portion of the solids recovered from the one or more recovery cyclones is discarded; wherein the catalytic pyrolysis is conducted at an operating temperature in the range from 300° C. to 800° C., or from 350° C. to 700° C., or from 400° C. to 650° C., or from 450° C. to 625° C., or from 500° C. to 600° C.; wherein a stream enriched in ethylene or propylene, or both is separated from the volatile products; wherein a stream enriched in ethylene or propylene, or both, is separated from the volatile products and is at least partially recycled to the pyrolysis reactor; wherein at least 80% of the mass of catalyst particles are at least 40 microns, or at least 50 microns, or at least 60 microns, or at least 75 microns, or at least 100 microns, or from 40 to 300 microns, or from 50 to 250 microns, or from 75 to 150 microns in size as measured by light scattering, X-ray diffraction (XRD), scanning electron microscopy (SEM), transmission electron microscopy (TEM), or scanning transmission electron microscopy (STEM); wherein at least 80% of the mass of filler particles are no more than 40 microns, or 30 microns, or 20 microns, or 15 microns, or 10 microns, or from 1 to 40 microns, or from 2 to 30 microns, or from 5 to 20 microns in size as measured by light scattering, X-ray diffraction (XRD), scanning electron microscopy (SEM), transmission electron microscopy (TEM), or scanning transmission electron microscopy (STEM); wherein the residence time of the fluidization gas in the catalytic pyrolysis reactor defined as the volume of the reactor divided by the volumetric flow rate of the fluidization fluid under method conditions of temperature and pressure, is from 1 second to 480 seconds, or from 1 second to 240 seconds, or from 2 seconds to 60 seconds, or from 3 seconds to 30 seconds, or from 4 seconds to 15 seconds; wherein the pressure in the fluidized bed reactor is at least 0.1 MPa, or at least 0.3 MPa, or at least 0.4 MPa, or from 0.1 to 2.0 MPa (1 to 20 bar), or from 0.1 to 1.0 MPa, or from 0.3 to 0.8 MPa, preferably from 0.4 to 0.6 MPa; wherein the fluidized bed reactor is a circulating bed, bubbling bed, turbulent bed or riser reactor; wherein the fluidization gas for the catalytic pyrolysis can comprise $H_2$, $CO$, $CO_2$, $H_2O$, C1-C4 paraffins or olefins or both, $N_2$, Ar, He, or a recycle stream, or some combination thereof; wherein the catalyst is a solid catalyst and the step of catalytically pyrolyzing comprises pyrolyzing in the presence of the solid catalyst in a fluidized bed reactor to produce a fluid product stream and used catalyst with coke, and wherein at least 90% the carbon in the feed is converted to coke and volatile products; wherein at least a portion of the separated catalyst from the low efficiency classifier cyclone is returned to the catalytic pyrolysis reactor, or passed to the catalyst regenerator, or discarded; wherein a catalyst and filler solids separation system comprising classifier cyclones and recovery cyclones is used, returning solids from the classifier cyclones to the fluidized bed reactor, and recovering olefins, or aromatics from the vapor exiting the last recovery cyclone; wherein the classifier cyclone is designed to have its cut size between the particle size distribution of the fillers and the particle size distribution of the catalyst allowing the larger particle size fraction to be separated and the smaller particle size fraction to be entrained in the off-gas for removal in a series of high efficiency recovery multiclones; wherein the feed mixture comprises plastics chosen from among polyethylene, polypropylene, polyesters, polyethylene terephthalate (PET), acrylonitrile-butadiene-styrene (ABS) copolymers, polyethylenefuranoate (PEF), polyamide, polyurethane, polyethers, polycarbonates, poly(oxides), poly(sulfides), polyarylates, polyetherketones, polyetherimides, polysulfones, polyurethanes, polyvinyl alcohols, and polymers produced by polymerization of monomers, such as, for example, dienes, olefins, styrenes, acrylates, acrylonitrile, methacrylates, methacrylonitrile, diacids and diols, lactones, diacids and diamines, lactams, vinyl esters, block copolymers thereof, and alloys thereof; thermoset polymers such as, for example, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, ethylene-propylene-diene monomer polymer; and mixtures thereof, wherein the feedstock comprises a mix of waste plastic chosen from among polyethylene terephthalate (PET), high density polyethylene (HDPE), polyvinyl chloride (PVC) or polyvinylidene (PVCD), low density polyethylene (LDPE), polypropylene (PP), polystyrene (PS), or mixed resins, or some combination thereof; wherein the feedstock comprises a mix of waste plastic chosen from among polyethylene terephthalate (PET), high density polyethylene (HDPE), polyvinyl chloride (PVC) or polyvinylidene (PVCD), low density polyethylene (LDPE), polypropylene (PP), polystyrene (PS), or mixed resins, or some combination thereof; wherein the filler is chosen from among alumina, aluminum, aluminum fiber, aluminum flakes, aluminum hydroxide, aluminum nitride, antimony doped tin oxide, antimony oxide, aramid, attapulgite, barium sulfate, barium titanate, bentonites, bismuth carbonate, boric oxide, boron nitride, bronze powder, calcium carbonate, calcium fluoride, calcium phosphate, calcium silicate, calcium sulfate, calcium sulfate whiskers, carbon black, carbon fiber, carbon nanotubes, cellulose nanocrystals, chitosan, clay, compatibilizers, copper, diamond, diatomaceous earth, expanded graphite, ferromagnetic powder, fluoromica, fly ash, fumed nanosilica, glass beads, glass fiber, glass flakes, glass spheres, graphene, graphite, ground tire rubber, hollow glass microspheres, hollow silicates, hydrotalcite, iron, kaolin, lignin, magnesium hydroxide, magnesium oxide, magnetite, mica, microfibrous cellulose, molybdenum sulfide, montmorillonite, nibatio3, nickel, phenolic microspheres, potassium titanate whisker, potassium-magnesium aluminosilicate, PTFE, pyrophyllite, red mud, red phosphorus, rubber particles, sand, sepiolite, silanes, silica, silicon carbide, silver powder, soot, starch, talc, tetrapod zinc oxide whisker, titania nanoparticles, titanium dioxide, vermiculite, wollastonite, wood fiber, wood flour, zinc borate, zinc oxide, zirconium silicate, or some combination thereof; wherein the filler is chosen from among calcium carbonate, carbon black, silica, kaolin clay, or talc, or some combination thereof. wherein the catalyst in the fluidized bed reactor comprises a zeolite; wherein the catalyst has a SAR (silica to alumina, $SiO_2$: $Al_2O_3$ mass ratio) greater than 12, or from 12 to 240, and a CI (constraint index) from 1 to 12 or from 5 to 10; wherein the zeolite catalyst is chosen from among ZSM-5, ZSM-11, ZSM-12, ZSM-22, ZSM-23, ZSM-35, ZSM-48, ZSM-50, or combinations thereof, wherein the catalyst comprises ZSM-5; wherein the catalyst in the fluidized bed comprises binder materials chosen from among alumina, zirconia, silica, magnesia, thoria, titania, boria, or combinations thereof, wherein the catalyst in the fluidized bed comprises a catalytic molecular sieve and wherein a catalytic molecular sieve comprises from 30 to 90 percent by weight or 40 to 70 percent by weight of the composition of the catalyst particles; wherein the catalyst in the fluidized bed is in the form of fluidizable microspheres; wherein the plastics are pretreated in a pyrolysis reactor to remove chlorine before being fed to the fluid bed catalytic pyrolysis reactor; wherein the pyrolysis reactor is a moving bed, one-screw extruder, two screw extruder, auger reactor, static mixer reactor, rotating kiln reactor, or a stepped grate reactor; wherein the pyrolysis reactor comprises a feed inlet port and an exit port and the temperature in the pyrolysis reactor ranges from a lower temperature near the feed entry port to a higher temperature at the exit port; wherein the temperatures in the pyrolysis reactor can be from 20° C. to 225° C., such as 20 to 100° C., or 20 to 50° C., at or near the inlet port, and the range of temperatures at the exit port can be from 300 C to 700° C., such as from 325 to 650° C., or from 350 to 600° C.; wherein the pyrolysis reactor comprises two or more reactors in series; wherein the residence time of condensed phases in the thermal treatment or pyrolysis reactor or reactors is at least 1, or at least 5, or at least 10, or at least 20, or at least 30, or from 1 to 60, or from 5 to 30, or from 10 to 30 minutes; wherein a vapor phase co-reactant comprising H2, CO, or olefins, or some combination of these, or a recycle stream is fed directly to the one or more pyrolysis reactors or the one or more catalytic pyrolysis reactors; wherein the product vapor mixture from the fluidized bed catalytic reactor comprises at least 10 mass % BTX, in some embodiments in the range of 10 to 90 mass % BTX; wherein the solid co-reactant fed to the thermal treatment reactor comprises agricultural lime, or calcium oxide, calcium hydroxide, magnesium oxide, magnesium hydroxide, limestone, hydrotalcites, activated carbon, or zeolite, or other solid basic material, or some combination thereof, wherein the product vapor mixture from the fluidized bed catalytic reactor comprises at least 10 mass % olefins, in some embodiments in the range of 10 to 90 mass % olefins; wherein the product vapor mixture from the fluidized bed catalytic reactor comprises at least 30%, or at least 40%, or at least 45%, or at least 50%, or at least 55%, or at least 60%, or from 20% to 90%, or from 30% to 70%, or from 45% to 60%, olefins based on the mass in the polymer feed; wherein the mass yield of BTX (benzene, toluene, and xylenes) in the product vapor mixture from the catalytic conversion is at least 30%, or at least 40%, or at least 45%, or at least 50%, or at least 55%, or at least 60%, or from 20% to 90%, or from 30% to 70%, or from 45% to 60%, BTX based on the mass in the polymer feed; wherein benzene, toluene, or xylenes are separated or recovered from the product vapor mixture; wherein at least a portion of the aromatic products in the product vapor mixture is hydrogenated to produce naphthenes; wherein ethylene, or propylene, or butenes, or some combination thereof is separated from the catalytic pyrolysis product vapor mixture; wherein the product vapor mixture is subjected to a separation method to produce a stream of gases enriched in $CH_4$, CO, and $H_2$; and passing at least a portion of the stream of gases enriched in $CH_4$, CO, and $H_2$ to the regenerator where they are combusted; wherein the product vapor mixture comprises $CH_4$ and $C_2$-$C_4$ paraffins; and wherein 50 to 100 mass % of the $CH_4$ and $C_2$-$C_4$ paraffins is combusted in the regenerator; wherein catalyst in the fluidized bed catalytic pyrolysis reactor is withdrawn and regenerated by oxidation with air or other oxidizing gas mixture and returned to the catalytic pyrolysis reactor; wherein the catalyst that is removed from the catalytic reactor, or the catalyst that is recovered in the solids separation system, or both is stripped of volatile materials by passing a stream of steam, nitrogen, CO, $CO_2$, $CH_4$, He, or some combination of these, or a recycle stream from the product gases through the catalyst particles; wherein condensable materials in the stream exiting the striper are condensed, the organic and aqueous phases are separated, the liquid organic phase is sent to product recovery, the aqueous phase is sent to wastewater recovery, and the catalyst that has been stripped of volatile organic compounds is sent to the catalyst regenerator; wherein the hot regenerated catalyst supplies heat to the catalytic pyrolysis reactor; wherein at least a portion of the gases in the product mixture are combusted in the regenerator; wherein at least a portion of natural gas is fed to the catalyst regenerator; wherein heat from the regeneration of the catalyst provides energy to the step of thermal treatment or pyrolyzing or catalytically pyrolyzing; wherein heat recovered from the catalyst regenerator is used to heat the feed materials, the thermal treatment reactor, or the pyrolysis reactor, or the catalytic pyrolysis fluidized bed reactor, or some combination thereof, wherein the combustion product gas (flue gas) that is produced in either the catalyst regenerator or filler regenerator or both is passed to a solids separation system, or to separate solids separation systems, the solids separation system or systems comprising a series of cyclones with an optional classifying cyclone followed by one or more high efficiency multiclones; wherein the flow velocity at the entrance of the low efficiency or classifier cyclone is greater than 5, or greater than 10, or greater than 15, or from 5 to 40, or from 10 to 30, or from 15 to 25 meters/second; wherein, in any of the classifier cyclones, the ratio of vortex diameter ["De" in FIG. 5] to cylinder internal diameter ("D" in FIG. 5) can be 0.2, or 0.3, or 0.4, or 0.5, or 0.6, or 0.7, or lie within the range from 0.1 to 0.8, or from 0.3 to 0.7, or from 0.4 to 0.6, or from 0.45 to 0.55, or from 0.49 to 0.51, or the ratio of vortex length to cylinder length can be 0.5, or 0.6, or 0.7, or 0.8, or 0.9, or lie within the range from 0.3 to 0.95, or from 0.5 to 0.95, or from 0.8 to 0.95, or from 0.85 to 0.95, or the ratio of underflow diameter to vortex diameter can be 0.02, or 0.1, or 0.15, or 0.2, or 0.25, or 0.3, or 0.5, or 1.0, or 1.25, or lie within the range from 0.02 to 1.25, or from 0.02 to 0.5, or from 0.1 to 0.3, or from 0.15 to 0.25, or the ratio of inlet height to inlet width can be 0.75, 1, or 1.5, or 2, or 2.4, or 3, or 4, or 5 or can lie within the range from 0.75 to 5, or from 1.5 to 4, or from 2 to 3, or from 2.2 to 2.6, or the ratio of vortex length (S) to total height (H) can be 0.1, or 0.2, or 0.3, or 0.36, or 0.4, or 0.5, or 0.6, or 0.8, or lie within the range from 0.1 to 0.8, or from 0.2 to 0.6, or from 0.3 to 0.4, or from 0.34 to 0.38; wherein one or more of the cyclones has no vortex finder; wherein the one or more recovery cyclones comprises at least one multiclone; wherein, for each of the multiple small diameter cyclones within any of the multiclones, the ratio of vortex diameter to cylinder diameter can be 0.2, or 0.3, or 0.4, or 0.5, or 0.6, or 0.7, or lie within the range from 0.1 to 0.8, or from 0.3 to 0.7, or from 0.4 to 0.6, or from 0.45 to 0.55, or from 0.49 to 0.51, or the ratio of vortex length to cylinder length can be 0.5, or 0.6, or 0.7, or 0.8, or 0.9, or lie within the range from 0.3 to 0.95, or from 0.5 to 0.95, or from 0.8 to 0.95, or from 0.85 to 0.95, or the ratio of underflow diameter to vortex diameter can be 0.02, or 0.1, or 0.15, or 0.2, or 0.25, or 0.3, or 0.5, or 1.0, or 1.25, or lie within the range from 0.02 to 1.25, or from 0.02 to 0.5, or from 0.1 to 0.3, or from 0.15 to 0.25, or the ratio of inlet height to inlet width can be 0.75, or 1, or 1.5, or 2, or 2.4, or 3, or 4, or 5 or can lie within the range from 0.75 to 5, or from 1.5 to 4, or from 2 to 3, or from 2.2 to 2.6, or the ratio of vortex length to total height can be 0.1, or 0.2, or 0.3, or 0.36, or 0.4, or 0.5, or 0.6, or 0.8, or lie within the range from 0.1 to 0.8, or from 0.2 to 0.6, or from 0.3 to 0.4, or from 0.34 to 0.38; wherein the flow velocity at the entrance of any of the recovery cyclones is no more than 25, or 20, or 15, or 10, or 5, or 3, or from 3 to 20, or from 5 to 15, or from 6 to 12 meters/second; wherein the mass ratio of catalyst particles to filler particles entering the classifier cyclone is at least 1, 2, 5, 10, 20, 30, or 50, or from 0.1 to 50, from 0.5 to 30, or from 5 to 20; wherein the mass ratio of catalyst particles to filler particles exiting the bottom of a classifier cyclone is at least 5, or at least 30, or at least 50, or at least 200, or at least 1000, or from 5 to 10,000, from 30 to 5,000, or from 50 to 1000; wherein the mass ratio of catalyst particles to filler particles in the overflow from a classifier cyclone is no more than 10, 5, 2, 1, 0.2, or 0.1, or from 0.0001 to 10, from 0.001 to 5, or from 0.01 to 1; wherein the mass ratio of catalyst particles to filler particles in the overflow from a recovery cyclone is no more than 0.1, 0.001, 0.00001, or from 0.0000001 to 0.1, from 0.00001 to 0.01, or from 0.0001 to 0.001; wherein the mass ratio of catalyst particles to filler particles in the bottoms from a recovery cyclone is no more than 0.1, 0.001, 0.00001, or from 0.0000001 to 0.1, from 0.00001 to 0.01, or from 0.0001 to 0.001; wherein the number of small cyclones within any one multiclone can be 4, 9, 16, 25, 36, 49, or 64, or from 4 to 64, or from 9 to 49, or from 16 to 36 cyclones; wherein the efficiency of the low efficiency or classifier cyclone or combination of cyclones is no more than 95%, or 90%, or 85%, or 80%, or 75%; wherein the efficiency of the one or more recovery cyclones taken together is at least 80%, or 85%, or 90%, or 95%, or 98%, or 99%, or 99.5%; wherein the concentration of particulates in the vapor product exiting the recovery cyclones is no more than 200, or 300, or 400, or 500 µg per m$^3$ of vapor product; wherein the plastics feed stream is treated in a thermal treatment reactor and the condensed phases are passed to the catalytic pyrolysis reactor; wherein a sweep gas such as $H_2O$, $N_2$, Ar, $CO_2$, or some combination thereof, is fed to the thermal treatment reactor and the vapors are exhausted; wherein the plastics feed stream is heated to a temperature between 25° and 300° C. in the thermal treatment reactor. and the products are passed to a pyrolysis reactor; wherein an inert gas is fed to the thermal treatment reactor and the vapors are exhausted; wherein the hot product stream from the thermal treatment reactor is filtered to remove solids before being fed to the pyrolysis reactor; wherein the products produced in the optional thermal treatment reactor are transferred, without separating a significant portion of the products, to a catalytic pyrolysis reactor containing a catalyst; wherein non-vapor products of the thermal treatment reactor, or a portion of the gases remaining after removal of desired products, or both, are combusted to provide energy for the catalytic reaction in the fluidized bed; wherein a solid co-reactant material is fed to the thermal treatment reactor; wherein the solid co-reactant material is separated from the method stream and transferred to a combustion regenerator wherein the carbonaceous materials are reacted with air and at least a portion of the hot solid co-reactant material is returned to the thermal treatment reactor; wherein the hot flue gas exiting the solid co-reactant material regenerator is passed to a catalyst heater to heat the catalyst for the catalytic pyrolysis reactor; wherein the thermal treatment is conducted by heating the feed to a temperature between 25° and 300° C., held at that temperature while vapors are removed, and then the condensed phases are sent to the catalytic pyrolysis reactor or further pyrolyzed at higher temperature in the pyrolysis reactor; wherein the catalyst that is removed from the catalytic reactor, or the catalyst that is recovered in the solids separation system, or both, are stripped of volatile materials by passing a stream of steam, nitrogen, CO, $CO_2$, $CH_4$, He, or some combination of these, or a recycle stream from the product gases through the catalyst particles, condensing the condensable materials in the stream, separating the organic and aqueous phases, sending the liquid organic phase to product recovery, sending the aqueous phase to wastewater recovery, and sending the catalyst that has been stripped of volatile organic compounds to the catalyst regenerator, or returned to the catalytic reactor, or discarded, or some combination thereof, wherein fillers are recovered from the solids separation system; wherein the fillers that are recovered in the solids separation system are stripped of volatile materials by passing a stream of steam, nitrogen, CO, $CO_2$, $CH_4$, He, or some combination of these, or a recycle stream from the product gases through the filler particles, condensing the condensable materials in the stream, separating the organic and aqueous phases, sending the liquid organic phase to product recovery, sending the aqueous phase to wastewater recovery, and sending the fillers that have been stripped of volatile organic compounds to the filler regenerator, or discarded, or some combination thereof.

There are many advantages of chemically recycling plastics by pyrolysis in a thermochemical reactor including a solids separation system: a mixture of any type of plastics is suitable, the plastic particles need not be ground to small size since the long residence time in the pyrolysis reactor or reactors ensures that the plastic pieces are heated to decomposition temperatures, the pyrolysis can be operated at high temperatures, undesirable contaminants can be removed in an optional thermal treatment reactor, small particle size fillers can be efficiently separated from catalyst and discarded, and the catalyst separated from the fillers can be returned to the process, reducing catalyst losses and the resulting catalyst costs. Another advantage of the inventive process is that the production of a crude liquid product stream made from recycled plastic by the inventive process can be conducted at a separate location from the product separation and purification system, and this "distributed processing" scheme minimizes the costs of separation and purification for small scale regional plastics upgrading facilities.

GLOSSARY

Figure 1:
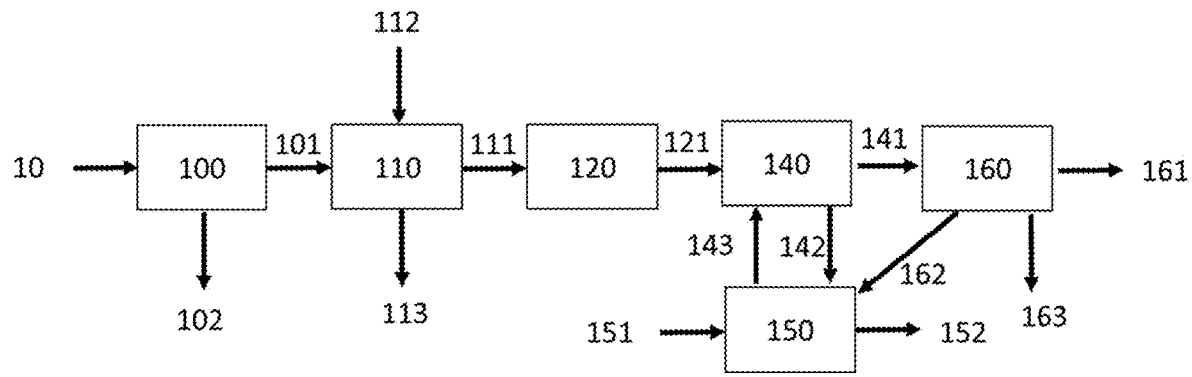
FIG. 1 schematically illustrates a process for converting mixed plastic materials to valuable products by pyrolyzing the mixed plastics and catalytically reacting the raw product mixture to produce olefins, aromatics, or some combination thereof that includes a solids separation system of cyclones to separate filler materials and other fines from the system.

Aromatics—As used herein, the terms "aromatics" or "aromatic compound" are used to refer to a hydrocarbon compound or compounds comprising one or more aromatic groups such as, for example, single aromatic ring systems (e.g., benzyl, phenyl, etc.) and fused polycyclic aromatic ring systems (e.g., naphthyl, 1,2,3,4-tetrahydronaphthyl, etc.). Examples of aromatic compounds include, but are not limited to, benzene, toluene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, xylenes (e.g., p-xylene, m-xylene, o-xylene, etc.), naphthalene, methyl-naphthalene (e.g., 1-methyl naphthalene, anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, and dimethyl-hydrindene. Single-ring and/or higher ring aromatics may also be produced in some embodiments.

Cyclone separators—In cyclone separators centrifugal force is used to separate solid from fluids. The separation process depends on particle size and particle density. It is also possible to allow fine particles to be carried with the fluid. A cyclone consists of a short vertical, cylindrical vessel with a conical base. The upper part of the vessel is fitted with a tangential inlet. The solid outlet is at the base. Fluid outlet is provided at the center of the top portion, which may extend inwardly into the separator, and such an arrangement prevents the gas short-circuiting directly from the inlet to the outlet of the fluid. The solids to be separated are suspended in a stream of gas that is introduced tangentially at a high velocity, so that rotary movement takes place within the vessel. The centrifugal force throws the particles to the wall of the vessel. As the speed of the gas diminishes, the larger, denser particles fall to the base and collect at the solid outlet. The gas can escape from the central outlet at the top with smaller, less dense particles entrained therein. The stream that exits the central outlet at the top of the cyclone is the overflow fraction and the stream that exits the solid outlet at the base is the underflow or bottoms fraction.

Catalysts—Catalyst components useful in the context of this invention can be selected from any catalyst known in the art, or as would be understood by those skilled in the art. Catalysts promote and/or affect reactions. Thus, as used herein, catalysts lower the activation energy (increase the rate) of a chemical process, and/or improve the distribution of products or intermediates in a chemical reaction (for example, a shape selective catalyst). Examples of reactions that can be catalyzed include: dehydration, dehydrogenation, isomerization, hydrogen transfer, hydrogenation, polymerization, cyclization, desulfurization, denitrogenation, deoxygenation, aromatization, decarbonylation, decarboxylation, aldol condensation, and combinations thereof. Catalyst components can be considered acidic, neutral, or basic, as would be understood by those skilled in the art.

For catalytic pyrolysis, particularly advantageous catalysts include those containing internal porosity selected according to pore size (e.g., mesoporous and pore sizes typically associated with zeolites), e.g., average pore sizes of less than about 10 nm, less than about 5 nm, less than about 2 nm, less than about 1 nm, less than about 0.5 nm, or smaller. In some embodiments, catalysts with average pore sizes of from about 0.5 nm to about 10 nm may be used. In some embodiments, catalysts with average pore sizes of between about 0.55 nm and about 0.65 nm, or between about 0.59 nm and about 0.63 nm may be used. In some cases, catalysts with average pore sizes of between about 0.7 nm and about 0.8 nm, or between about 0.72 nm and about 0.78 nm may be used.

In some preferred embodiments of catalytic pyrolysis, the catalyst may be selected from naturally occurring zeolites, synthetic zeolites and combinations thereof. In certain embodiments, the catalyst may be a ZSM-5 zeolite catalyst, as would be understood by those skilled in the art. Optionally, such a catalyst can comprise acidic sites. Other types of zeolite catalysts include: ferrierite, zeolite Y, zeolite beta, mordenite, MCM-22, ZSM-23, ZSM-57, SUZ-4, EU-1, ZSM-11, (S)AlPO-31, SSZ-23, among others. Zeolites and other small pore materials are often characterized by their Constraint Index. The Constraint Index approximates the ratio of the cracking rate constants for normal hexane and 3-methylpentane. The method by which Constraint Index is determined is described more fully in U.S. Pat. No. 4,029,716, incorporated by reference for details of the method.

Constraint Index (CI) values for some typical materials are:

TABLE 1

Constraint Indices of some common zeolites.

| Material | Constraint Index | Test Temp, ° C. |
|---|---|---|
| ZSM-4 | 0.5 | 316 |
| ZSM-5 | 6-8.3 | 371-316 |
| ZSM-11 | 5-8.7 | 371-316 |
| ZSM-12 | 2.3 | 316 |
| ZSM-20 | 0.5 | 371 |
| ZSM-22 | 7.3 | 427 |
| ZSM-23 | 9.1 | 427 |
| ZSM-34 | 50 | 371 |
| ZSM-35 | 4.5 | 454 |
| ZSM-48 | 3.5 | 538 |
| ZSM-50 | 2.1 | 427 |
| Mordenite | 0.5 | 316 |
| REY | 0.4 | 316 |
| Dealuminized Y | 0.5 | 510 |
| Beta | 0.6-2 | 316-399 |

The CI may vary within the indicated range of 1 to 12. Likewise, other variables such as crystal size or the presence of possibly occluded contaminants and binders intimately combined with the crystal may affect the CI. It is understood to those skilled in the art that the CI, as utilized herein, while affording a highly useful means for characterizing the molecular sieves of interest is approximate, taking into consideration the manner of its determination, with the possibility, in some instances, of compounding variable extremes. However, the CI will have a value for any given molecular sieve useful herein within the approximate range of 1 to 12.

In other embodiments, non-zeolite catalysts may be used; for example, WOx/ZrO2, aluminum phosphates, etc. In some embodiments, the catalyst may comprise a metal and/or a metal oxide. Suitable metals and/or oxides include, for example, nickel, palladium, platinum, titanium, vanadium, chromium, manganese, iron, cobalt, zinc, copper, gallium, and/or any of their oxides, among others. In some cases, promoter elements chosen from among the rare earth elements, i.e., elements 57-71, cerium, zirconium or their oxides for combinations of these may be included to modify activity or structure of the catalyst. In addition, in some cases, properties of the catalysts (e.g., pore structure, type and/or number of acid sites, etc.) may be chosen to selectively produce a desired product.

Catalysts for other processes, such as alkylation of olefins, aromatization (hydrocarbon reforming), hydrogenation, hydrotreating, deoxygenation, denitrogenation, and desulfurization are well-known and can be selected for the olefin conversion or other processes described herein. Plastics or Polymers—The terms "plastics" and "polymers" are used interchangeably herein. A polymer is a carbon-based (typically at least 50 mass % C) material chiefly made up of repeating units and having a number average molecular weight of at least 100, typically greater than 1000 or greater than 10,000. Polymers include thermoplastic polymers such as, for example, polyethylene, polypropylene, polyesters, polyethylene terephthalate (PET), acrylonitrile-butadiene-styrene (ABS) copolymers, polyethylenefuranoate (PEF), polyamide, polyurethane, polyethers, polycarbonates, poly (oxides), poly(sulfides), polyarylates, polyetherketones, polyetherimides, polysulfones, polyurethanes, polyvinyl alcohols, and polymers produced by polymerization of monomers, such as, for example, dienes, olefins, styrenes, acrylates, acrylonitrile, methacrylates, methacrylonitrile, diacids and diols, lactones, diacids and diamines, lactams, vinyl halides, vinyl esters, block copolymers thereof, and alloys thereof, thermoset polymers such as, for example, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, ethylene-propylene-diene monomer polymer; and blends thereof. Mixtures of polymers separated from municipal solid waste or other waste streams are suitable feeds provided they contain only small fractions of contaminants such as S, N, O, halogens, minerals, metals, or carbon black. Polymers yielding halogenated material upon pyrolysis, for example, polyvinyl chloride (PVC), polytetrafluoroethylene (PTFE), and other halogenated polymers, are generally minimized or excluded from the feed materials useful in this invention. Pyrolysis— The terms "pyrolysis" and "pyrolyzing" are given their conventional meaning in the art and are used to refer to the transformation of a compound, e.g., a solid hydrocarbonaceous material, into one or more other substances, e.g., volatile organic compounds, gases and coke, by heat, preferably without the addition of, or in the absence of, $O_2$. Preferably, the volume fraction of $O_2$ present in a pyrolysis reaction chamber is 0.5% or less. Pyrolysis may take place with or without the use of a catalyst. "Catalytic pyrolysis" refers to pyrolysis performed in the presence of a catalyst and may involve steps as described in more detail below. Example of catalytic pyrolysis processes are outlined, for example, in Huber, G. W. et al, "Synthesis of Transportation Fuels from Biomass: Chemistry, Catalysts, and Engineering," *Chem. Rev.* 106, (2006), pp. 4044-4098.

A "classifier cyclone" is a type of cyclone separator that is used to separate solid particles from a gas or vapor stream based on the particle size and density. The classifier cyclone works by using centrifugal force to separate a fraction of the particles as defined by the cut size from the gas stream. As the gas and particles enter the cyclone, the spinning motion creates a vortex, which causes the heavier particles to move towards the wall of the cyclone and the lighter particles to remain in the center. The separated particles then exit the cyclone through a separate outlet, while the gas or vapor continues to flow through the cyclone along with the remaining particles and exits through a different outlet.

A "recovery cyclone" is a type of cyclone that separates solids from a vapor stream that removes a sufficient fraction of the solids to permit the vapor stream to be processed in conventional condensation, distillation, or upgrading equipment in a chemical process. Typical recovery cyclones remove enough particles such that the concentration of particulates in the vapor product exiting the recovery cyclone(s) is less than some target concentration, e.g. no more than 200, or 300, or 400, or 500 μg per m$^3$ of vapor product.

Cyclone separation efficiency (sometimes called recovery) is the percentage of a selected cumulative fraction of solids in a stream that goes to either product. Efficiency, E, (or overall efficiency) is the difference between fine and coarse product recoveries, calculated as follows:

$$E=E_P \cdot E_T=(X_P \cdot W_P - X_T \cdot W_T)/X_F \cdot W_F$$

Where P indicates product, T indicates tailings (or fines), and F indicates feed, X is the mass fraction of particles of a certain size, and W is the mass of particles of a certain size, as described in Klumpar, V. I., "Measuring and Optimizing Air Classifier Performance," *Sep. Technol.*, 2, 1992, 124-135.

A cyclone that has a low efficiency, i.e., a significant portion of the solids entering the cyclone is passed through the cyclone and out with the overflow fraction, is referred to as a classifier cyclone. A classifier cyclone can be used to separate materials with different average particle sizes. A cyclone that has a high efficiency, i.e., only a small portion of the solids entering the cyclone is passed through the cyclone and out with the overflow fraction, is referred to as a recovery cyclone since its purpose is to remove solids from the vapor stream.

Cut size—During a particle size separation process, the term 'cut size' (or d50) is the particle size at which there is equal chance that the particle will report to the overflow or underflow. The value of dX indicates particle size with the probability X % that will be removed with the underflow of solids that exit the bottom of the cyclone rather than the overflow of gas that contains entrained solids. A partition curve presents the mass fraction for each particle size which is discharged in the coarse product (underflow or bottoms).

Fillers—The term "fillers" refers to any solid material that is added to or is part of a polymer composition in amounts up to 20% by weight, for example alumina, aluminum, aluminum fiber, aluminum flakes, aluminum hydroxide, aluminum nitride, antimony doped tin oxide, antimony oxide, aramid, attapulgite, barium sulfate, barium titanate, bentonites, bismuth carbonate, boric oxide, boron nitride, bronze powder, calcium carbonate, calcium fluoride, calcium phosphate, calcium silicate, calcium sulfate, calcium sulfate whiskers, carbon black, carbon fiber, carbon nanotubes, cellulose nanocrystals, chitosan, clay, compatibilizers, copper, diamond, diatomaceous earth, expanded graphite, ferromagnetic powder, fluoromica, fly ash, fumed nanosilica, glass beads, glass fiber, glass flakes, glass spheres, graphene, graphite, ground tire rubber, hollow glass microspheres, hollow silicates, hydrotalcite, iron, kaolin, lignin, magnesium hydroxide, magnesium oxide, magnetite, mica, microfibrous cellulose, molybdenum sulfide, montmorillonite, Ni—BaTiO$_3$, nickel, phenolic microspheres, potassium titanate whisker, potassium-magnesium aluminosilicate, PTFE, pyrophyllite, red mud, red phosphorus, rubber particles, sand, sepiolite, silanes, silica, silicon carbide, silver powder, soot, starch, talc, tetrapod zinc oxide whisker, titania nanoparticles, titanium dioxide, vermiculite, wollastonite, wood fiber, wood flour, zinc borate, zinc oxide, zirconium silicate, or any combination thereof.

Fluid—The term "fluid" refers to a gas, a liquid, a mixture of a gas and a liquid, or a gas or a liquid containing dispersed solids, liquid droplets and/or gaseous bubbles. The terms "gas" and "vapor" have the same meaning and are sometimes used interchangeably. In some embodiments, it may be advantageous to control the residence time of the fluidization fluid in the reactor. The fluidization residence time of the fluidization fluid is defined as the volume of the reactor divided by the volumetric flow rate of the fluidization fluid under process conditions of temperature and pressure.

Fluidized Bed Reactor—The term "fluidized bed reactor" is given its conventional meaning in the art and is used to refer to reactors comprising a vessel that can contain a granular solid material (e.g., silica particles, catalyst particles, etc.), in which a fluid (e.g., a gas or a liquid) is passed through the granular solid material at velocities sufficiently high as to suspend the solid material and cause it to behave as though it were a fluid. Examples of fluidized bed reactors are described in "Fluidization Engineering" by D. Kunii and O. Levenspiel, Butterworth-Heinemann, 1991, incorporated herein by reference. The term "circulating fluidized bed reactor" is also given its conventional meaning in the art and is used to refer to fluidized bed reactors in which the granular solid material is passed out of the reactor, circulated through a line in fluid communication with the reactor, and recycled back into the reactor. Examples of circulating fluidized bed reactors are described in "Fluidization Engineering" by D. Kunii and O. Levenspiel, Butterworth-Heinemann, 1991.

Bubbling fluidized bed reactors and turbulent fluidized bed reactors are also known to those skilled in the art. In bubbling fluidized bed reactors, the fluid stream used to fluidize the granular solid material is operated at a sufficiently low flow rate such that bubbles and voids are observed within the volume of the fluidized bed during operation. In turbulent fluidized bed reactors, the flow rate of the fluidizing stream is higher than that employed in a bubbling fluidized bed reactor, and hence, bubbles and voids are not observed within the volume of the fluidized bed during operation. Examples of bubbling and turbulent fluidized bed reactors are described in *Kirk-Othmer Encyclopedia of Chemical Technology* (online), Vol. 11, Hoboken, N.J.: Wiley-Interscience, 2001, pages 791-825, incorporated herein by reference.

Olefins—The terms "olefin" or "olefin compound" (a.k.a. "alkenes") are given their ordinary meaning in the art and are used to refer to any unsaturated hydrocarbon containing one or more pairs of carbon atoms linked by a double bond. Olefins include both cyclic and acyclic (aliphatic) olefins, in which the double bond is located between carbon atoms forming part of a cyclic (closed-ring) or of an open-chain grouping, respectively. In addition, olefins may include any suitable number of double bonds (e.g., monoolefins, diolefins, triolefins, etc.). Examples of olefin compounds include, but are not limited to, ethene, propene, allene (propadiene), 1-butene, 2-butene, isobutene (2 methyl propene), butadiene, and isoprene, among others. Examples of cyclic olefins include cyclopentene, cyclohexane, cycloheptene, among others. Aromatic compounds such as toluene are not considered olefins; however, olefins that include aromatic moieties are considered olefins, for example, benzyl acrylate or styrene.

"Thermal treatment" is used herein as a process for heating a feed mixture to modest temperature at which some contaminants such as HCl, H$_2$S, NH$_3$ are evolved and can be exhausted, and the feed mixture becomes molten so that solids such as minerals, metals, and carbon black can be removed by filtration.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of" As used in this specification, the terms "includes" or "including" should not be read as limiting the invention but, rather, listing exemplary components.

DETAILED DESCRIPTION OF THE INVENTION

FIG. 1 presents a schematic of a process for converting plastic waste to olefins and aromatics. A mixture of plastics 10 is introduced into an optional feed system 100 that prepares the plastic mixture for introduction into the process by, for example, removing undesirable feed materials 102 such as metal, minerals, clay, halogenated materials, contaminants such as Cl, Br or other elements that may poison the catalyst, and the like, or sizing the material to the desired size range, or both. The steps of removal of undesirable feed materials and sizing can be conducted in any order, i.e., either step can be conducted first and the other step conducted second. The remaining plastic mixture 101 can be passed to an optional washing process 110 wherein the plastic mixture may be washed for example by treatment with a wash solution 112 to remove unwanted materials such as dirt, or labels, or coatings, or the like, to produce washed plastic mixture 111 and used solution 113. The plastic mixture 111 is passed to optional pyrolysis reactor 120. Optionally a vapor phase co-reactant comprising H2, CO, or olefins, or some combination of these, or a recycle stream (not shown) can be fed directly to the optional pyrolysis reactor 120 or to the catalytic pyrolysis reactor 140. In the optional pyrolysis reactor 120 the mixture may be heated to a temperature to decompose the plastics into a product mixture comprising a combination of vapor, solid and liquid phases. Without separation, at least a portion of the raw pyrolysis product mixture 121 is passed to catalytic reactor 140 while maintaining the temperature of the pyrolysis product mixture at least at the temperature at which it left the pyrolysis reactor 120. The plastic mixture, either the raw plastic mixture 101, or the washed plastic mixture 111, or the pyrolysis product mixture 121, is passed to a hot catalytic reactor 140 that is charged with an aromatization catalyst effective at converting paraffins, or olefins, or both to aromatics, shown as catalytic vapor stream 141. A portion of the catalyst 142 is continuously withdrawn from reactor 140, or can be separated from the product 141, or both, and passed to catalyst regenerator 150. In catalyst regenerator 150 the catalyst is oxidized by treatment with a source of oxygen such as air 151, the hot regenerated catalyst 143 is returned to reactor 140 to provide heat for the reactor, and the combustion product gases 152 are sent to the regenerator flue gas purification cyclones (not shown) or vented or used to provide heat to the optional pyrolysis reactor or reactors or catalytic pyrolysis reactor or reactors. Catalytic vapor stream 141 is passed to solids separation system 160 wherein catalyst 162 is separated from fillers 163 and catalytic product stream 161. Catalyst 162 can be returned to the reactor 140 or passed to the catalyst regenerator 150 or discarded. Fillers 163 can be passed to a filler regenerator (not shown) or discarded. Catalytic product stream 161 can be separated into components such as ethylene, propylene, butenes, C1-C5 paraffins, benzene, toluene, xylenes, naphthalene, and other fractions in a separation scheme using conventional separation techniques not shown here.

Figure 2:
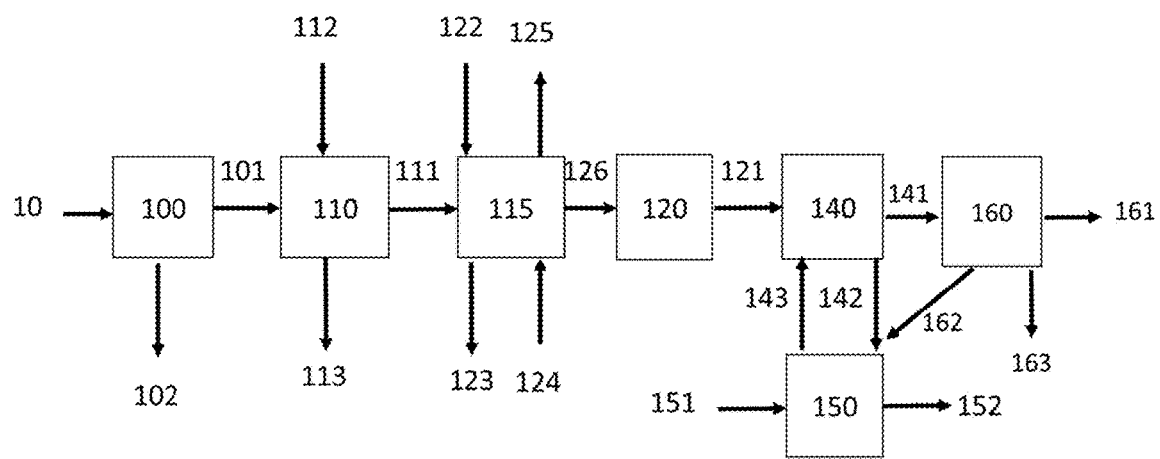
FIG. 2 schematically illustrates a process for converting mixed plastic materials to valuable products by pyrolyzing the mixed plastics and catalytically reacting the products to produce olefins, aromatics, or some combination thereof, wherein a thermal treatment reactor is used to remove contaminants before feeding the pyrolysis reactor, and wherein a solids separation system separates filler materials and other fines from the system.

FIG. 2 presents a schematic of another embodiment of the inventive process for converting plastic waste to olefins and aromatics. A mixture of plastics 10 is introduced into an optional feed system 100 that prepares the plastic mixture for introduction into the process by, for example, removing undesirable feed materials 102 such as metal, minerals, clay, halogenated materials, contaminants such as Cl, Br or other elements that may poison the catalyst, and the like, or sizing the material to the desired size range, or both. The steps of removal of undesirable feed materials and sizing can be conducted in any order, i.e., either step can be conducted first and the other step conducted second. The remaining plastic mixture 101 is passed to an optional washing process 110 wherein the plastic mixture may be washed for example by treatment with a wash solution 112 to remove unwanted materials such as dirt, or labels, or coatings, or the like, to produce washed plastic mixture 111 and used solution 113. The prepared plastic mixture 111 is passed to thermal treatment reactor 115 with optional co-reactant 122 such as a heat transfer medium or getter or the like, where the mixture is heated to an intermediate temperature to partially decompose the plastics, e.g. decompose PVC or PVDC to release HCl, or decompose another halogenated polymer to release HCl, HBr, or HI, or release vapors such as $NH_3$, $H_2O$, or the like. An optional sweep gas 124 such as $H_2O$, $N_2$, Ar, CO2, or some combination thereof is fed to thermal treatment reactor 115 to aid in the removal of vapors produced therein which are exhausted through exit port 125. With or without a sweep gas, the vapor 125 can be treated to capture or neutralize HCl and toxic materials prior to release or transfer to water treatment. The vapor 125 typically comprises at least 60% or at least 80% $H_2O$, and may contain HCl, halogenated carbon compounds, and other species more volatile than molten polymers. The condensed phases 126 may be passed to optional pyrolysis reactor 120 where they are heated to decompose into a product mixture comprising a combination of solid, liquid, and vapor phases. When an optional pyrolysis reactor is used, the temperature of the pyrolysis product mixture is maintained at least at the temperature at which it left pyrolysis reactor 120. The plastic feed mixture, or the raw product mixture 121 when optional pyrolysis reactor 120 is used, is passed to hot catalytic reactor 140 that is charged with an aromatization catalyst effective at converting paraffins, or olefins, or both to aromatics, shown as catalytic vapor stream 141. A portion of the catalyst 142 can be continuously withdrawn from reactor 140, or can be separated from the product 141, or both, and at least a portion thereof passed to catalyst regenerator 150. In catalyst regenerator 150 the catalyst is oxidized by treatment with a source of oxygen such as air 151 and the regenerated catalyst 143 is returned to reactor 140 and the combustion product gases 152 are sent to the regenerator cyclones (not shown) or vented. Optionally, natural gas or a recycle stream can be fed to catalyst regenerator 150 to raise the temperature of the regenerated catalyst to that desired for the catalytic pyrolysis process. Catalytic vapor stream 141 is passed to solids separation system 160 wherein catalyst 162 is separated from fillers 163 and catalytic product stream 161. At least a portion of catalyst 162 can be returned to the reactor 140 or can be passed to the catalyst regenerator 150 or discarded. Fillers 163 can be passed to a filler regenerator (not shown) wherein the fillers are oxidized with air or oxygen to generate heat that can be used in the process, or discarded. Catalytic product 141 can be separated into components such as ethylene, propylene, butenes, C1-C5 paraffins, benzene, toluene, xylenes, naphthalene, and other fractions in a separation scheme using conventional separation techniques.

Figure 3:
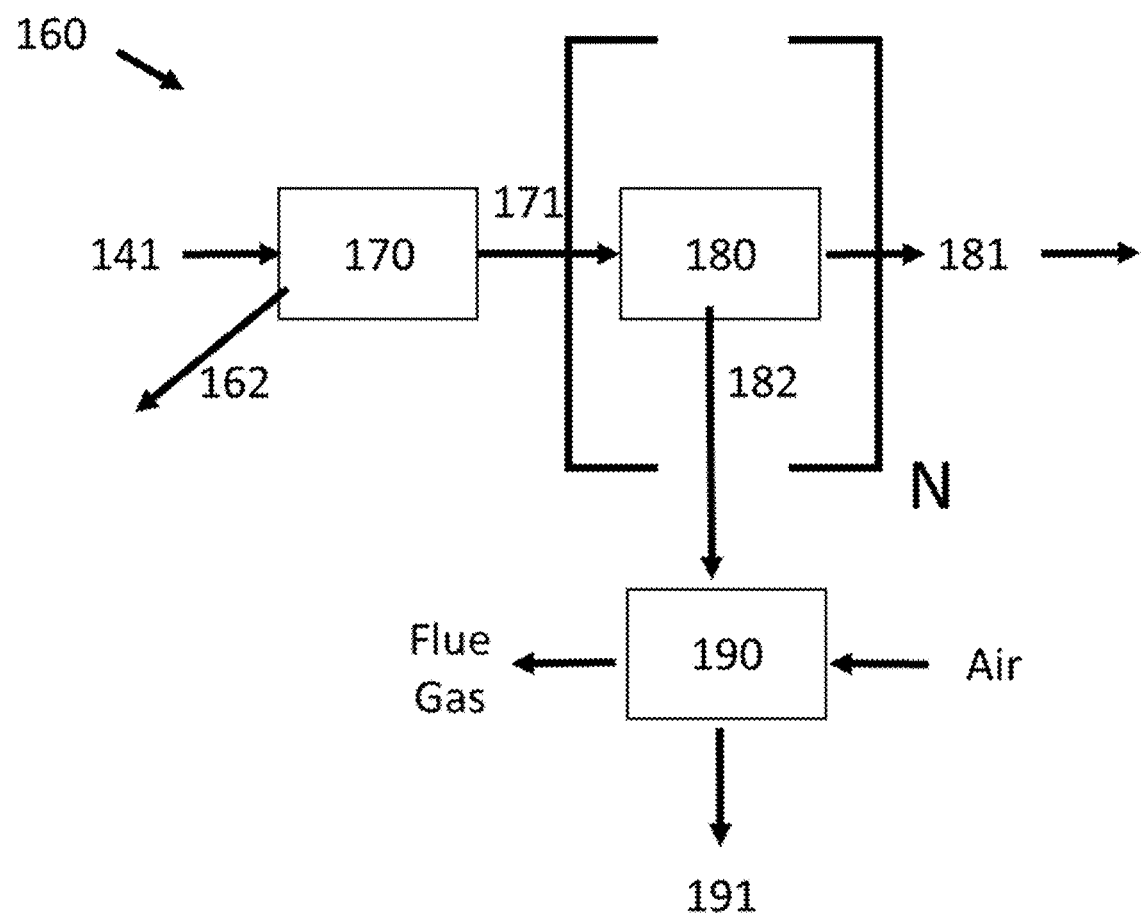
FIG. 3 presents a schematic of a solids separation system.

FIG. 3 presents a schematic of a solids separation system 160 in more detail. Catalytic vapor stream 141 that contains entrained catalyst and fillers is sent to one or more classifying (low efficiency) cyclones 170 where catalyst 162 that contains a small portion of filler particles is separated and sent to catalyst regeneration 150, or to the catalytic pyrolysis reactor 140, or discarded, or some combination of these. The vapor stream 171 that exits classifier 170 entrains most of the filler and almost no catalyst except some fines. The vapor stream 171 is sent to a series (N units) of high efficiency multiclones 180 wherein fillers 182 are separated and optionally sent to filler regenerator 190 where they are combusted with air to provide heat for the process or are discarded. The regenerated filler materials 191 are discarded. Product stream 181 that has had most of the filler removed is sent to separation and product collection; it contains a concentration of solids that does not exceed the allowable limit of entrained particles for emission to the atmosphere.

The solids separation system of the invention provides a means of separating filler material from catalyst wherein the filler material has a cut size or particle size that is smaller than the cut size or particle size of the fluid bed catalyst. The vapor effluent from the catalytic pyrolysis comprising catalyst particles and filler material is passed through a first cyclone to separate a first bottoms fraction and a first overflow fraction. The bottoms fraction from the first cyclone has a mass ratio of catalyst to filler that is greater than the mass ratio of the catalyst to filler in the effluent from the catalytic pyrolysis reactor, i.e., it is enriched in catalyst. The overflow fraction from the first cyclone is passed into a second cyclone that has a separation efficiency for the catalyst particles that is greater than the first separation efficiency, to separate a second bottoms fraction and a second overflow fraction. The bottoms fraction from the second cyclone has a catalyst to filler mass ratio that is less than the mass ratio in the effluent from the catalytic pyrolysis reactor, i.e., it is enriched in filler material. It is recognized that the first cyclone can include more than one cyclone, and that the second cyclone can include more than one cyclone.

The exhaust gas from the catalyst regenerator or filler regenerator can be passed through one or more cyclones to remove particulate matter therefrom. Optionally, where the exhaust gas from the catalyst regenerator contains catalyst particles that are desired to be recovered, the exhaust gas from the catalyst regenerator can be subjected to a series of cyclones that comprises a classifying cyclone and one or more purification cyclones. Catalyst particles recovered from the classifying cyclone can be returned to the catalytic pyrolysis reactor. Smaller particles recovered from purification stage or stages can be discarded.

Combustible gases such as methane, ethane, propane, butanes, CO and $H_2$, optionally, can be recovered from vapor stream 125 or recovered from the gases produced in the catalytic pyrolysis in the fluidized bed reactor or from the product stream 141. Combustible gases can provide heat for the process. Heat required for the catalytic pyrolysis process reactor 140 or optional pyrolysis reactor 120 or both can be provided at least in part by the hot regenerated catalyst 143. Heat in reactors 115 or 120 may also be provided by pressure/friction and/or other heat sources such as resistive or inductive heating.

In some embodiments, for example when recycled polymeric materials are used, impurities may optionally be removed from the feed composition prior to being fed to the reactor, e.g., by an optional separation step such as 100 in FIG. 1 or FIG. 2. In some instances, the separation step may include mechanical separation, sink/float separation, air elutriation, or other known separation processes, preferably in an automated mode. The particle size of the solid polymer feed composition may be reduced in a size reduction system as part of 100 prior to passing the feed to the thermal treatment reactor or pyrolysis reactor. In some embodiments, the average diameter of the reduced size feed composition exiting the size reduction system may comprise no more than 50%, no more than 25%, no more than 10%, no more than 5%, or no more than 2% of the mass average diameter of the feed composition fed to the size reduction system. The feed mixture may comprise plastics mixtures in which at least 85% by mass, or at least 90% by mass, or at least 95% by mass of the particles pass through a 0.25 inch (0.6 cm), or 0.5 inch (1.2 cm), or 1.0 inch (2.5 cm), or 1.5 inch (3.7 cm), or 2 inch (5.0 cm), or 4 inch (10.0 cm) screen. Average diameter (size) can be determined by sieving through mesh (screen). Large-particle feed material may be more easily transportable and less difficult to process than small-particle feed material. On the other hand, in some cases it may be advantageous to feed small particles to the reactor. The use of a size reduction system allows for the transport of large-particle feed between the source and the process, while enabling the feed of small particles to the reactor.

The feed materials suitable for use in the invention can comprise all types of polymeric materials including polyethylene (PE), polypropylene (PP), polyacetylene, polybutylene, polyolefins, polyethylene terephthalate (PET), polybutylene terephthalate, polyester, copolyesters, polycarbonate, polyurethanes, polyamides, polystyrene (PS), polyacetal, epoxies, polycyanurates, polyacrylics, polyurea, vinyl esters, polyacrylonitrile, polyamide, polyurethane, polyethers, polycarbonates, poly(oxides), poly(sulfides), polyarylates, polyetherketones, polyetherimides, polysulfones, polyurethanes, polyvinyl alcohol, polyvinylchloride (PVC), polyvinyl dichloride (PVDC), polyvinyl acetate, nylon, copolymers such as ethylene-propylene, acrylonitrile-butadiene-styrene (ABS), nitrile rubber, natural and synthetic rubber, tires, styrene-butadiene, styrene-acrylonitrile, styrene-isoprene, styrene-maleic anhydride, ethylene-vinyl acetate, nylon 12/6/66, filled polymers, polymer composites, plastic alloys, other polymeric materials, and polymers or plastics dissolved in a solvent, whether obtained from polymer or plastic manufacturing processes as waste or discarded materials, post-consumer recycled polymer materials, materials separated from waste streams such as municipal solid waste, and polymers produced by polymerization of monomers, such as, for example, dienes, olefins, styrenes, acrylates, acrylonitrile, methacrylates, methacrylonitrile, diacids and diols, lactones, diacids and diamines, lactams, vinyl esters, block copolymers thereof, and alloys thereof, thermoset polymers such as, for example, epoxy resins; phenolic resins; melamine resins; alkyd resins; vinyl ester resins; unsaturated polyester resins; crosslinked polyurethanes; polyisocyanurates; crosslinked elastomers, including but not limited to, polyisoprene, polybutadiene, styrene-butadiene, styrene-isoprene, or some combination of these. The invention includes subcombinations of these materials, as desired, or as available from a particular location; the invention can be described as comprising one or any combination of these materials.

In any of the methods, the thermal treatment reactor 115 or pyrolysis reactor 120, or more than one of these, can be a moving bed reactor wherein the feed material is impelled along the length of the reactor by mechanical or gravitational means or both mechanical and gravitational means. Typical examples of reactors suitable for the thermal treatment reactor 115 or pyrolysis reactor 120, include a 1-screw extruder, 2-screw extruder, auger reactor, static mixer reactor, rotating kiln reactor, or stepped grate reactor. In any of the embodiments the pyrolysis reactor may have multiple heating zones with successively higher temperatures in later zones. In some embodiments the thermal treatment reactor or pyrolysis reactor is fitted with a gas outlet at an area of the reactor where the temperature of the materials in the reactor is less than 300° C. or between 250° C. and 300° C. to allow for the removal of products produced at low temperatures such as steam, HCl, $NH_3$, or other materials from the reactor. A separating screen can be fitted within the pyrolysis reactor immediately downstream of the gas outlet to at least partially prevent gases evolved at low temperature from passing along with the molten and solid materials into the hotter portions of the reactor. A gas inlet for the introduction of hot inert or recycle gas such as a gas comprising any of $CH_4$, $H_2$, CO, $CO_2$, and $C_2$-$C_4$ paraffins or olefins, or a mixture, can be fitted immediately downstream of the gas vent and optional screen.

Optionally, solid co-reactants 122, such as CaO, MgO, hydrotalcites, activated carbon, or zeolites, or some combination of these, that trap or remove undesirable components can be fed to thermal treatment reactor 115 and separated therefrom by filtration through a screen.

Where an auger reactor is utilized for thermal treatment or pyrolysis, these can include helical augers that optionally have different pitch dimensions at different portions of the auger in order to adjust the velocity of the condensed phases from the entry to the exit of the reactor. The flight thickness and shaft diameter may also be of variable dimension along the length of the auger in order to control the flow velocity of the vapor and condensed phases. Augers with paddles, or cuts, or folded flights are also envisioned as within the scope of the invention.

A rotating kiln reactor can be utilized for thermal treatment or pyrolysis, the kiln cylinder can be fitted with lifters, such as helical lifters attached to the cylinder wall or tabular lifters, folded lifters, or segmented lifters extending from the cylinder wall. A rotating kiln reactor can also be inclined either up or down towards the exit end of the kiln depending on the desired residence time and flow velocity desired for the condensed phases within the kiln, thus taking advantage of gravity to control residence time of the condensed phases. The rotation rate of the rotating kiln reactor can be adjusted as desired, for example between 20 revolutions per minute to 0.2 revolution per minute depending on the nature of the feed mixture and the co-reactant added in order to provide thorough mixing and high heat transfer. A rotating kiln reactor can be heated externally with combustion of waste process gases such as $CH_4$, $C_2$-$C_4$ paraffins, $H_2$, CO, and the like recycled from the product separation or natural gas or electrically.

In any of the inventive aspects, the temperature profile within the optional pyrolysis reactor can range from a lower temperature near the feed entry port to a higher temperature at the exit port or ports. The range of temperatures can be from 20° C. to 225° C., such as 20 to 100° C., or 20 to 50° C., at or near the inlet port, and the range of temperatures at the high temperature exit port can be from 300° C. to 700° C., such as from 325 to 650° C., or from 350 to 600° C. A solid co-reactant can be fed to the thermal treatment reactor and the solid co-reactant material optionally transferred to a combustion regenerator wherein the carbonaceous materials are reacted with air and at least a portion of the hot solid co-reactant material is returned to the thermal treatment reactor. The hot flue gas exiting the solid co-reactant regenerator can be passed to a catalyst heater to heat the catalyst for the catalytic pyrolysis reactor.

After leaving the thermal treatment reactor 115, the raw product preferably does not contact any cool surfaces that could condense products, and the surfaces are preferably maintained at a temperature of at least 300° C., at least 325, or at least 350° C. or within 25 or 50° C. of the temperature exiting the reactor 115. Preferably, in any of the embodiments, the temperature of the mixture is maintained at a temperature at least 2° C., or at least 3° C., or at least 5° C., or at least 10° C. higher than the temperature of the mixture at the exit end of the thermal treatment reactor.

In any of the inventive aspects, the catalytic reactor 140 can be a fluidized bed reactor; wherein the catalyst is a solid catalyst and the step of catalytically pyrolyzing comprises pyrolyzing in the presence of the solid catalyst in a fluidized bed reactor to produce a fluid product stream 141 and used catalyst with coke 142; and wherein at least a portion of the used catalyst with coke is transferred to a regenerator 150 where the coke is reacted with oxygen or air to form hot regenerated catalyst, and returning at least a portion of the hot regenerated catalyst 143 to the fluidized bed reactor, wherein heat from the hot regenerated catalyst provides energy to the step of catalytic pyrolyzing.

The vapors exiting the catalytic pyrolysis reactor are passed through a solids separation system comprising a series of cyclones to separate entrained solids into larger particle size and smaller particle size fractions. In any of the methods the solids separation system comprises a series of one or more cyclones and one or more multicyclones. The first cyclone in the series is typically a relatively low efficiency classifier type cyclone that makes a rough separation of smaller from larger particles.

Cyclones are typically designed and installed in order to separate solids as efficiently as possible from the gas stream such as when dust is removed from flue gas. The overall cyclone separation efficiency is defined as the ratio of the solids mass flow rate from the bottom of the cyclone to the solids mass flow rate at the cyclone inlet, an efficiency of 1 indicates that there are no solids exiting with the gas at the top of the cyclone, an efficiency of 0.99 indicates that 0.01 of the solids are exiting with the gas at the top of the cyclone etc. Therefore, for a bimodal solids stream entering the cyclone with a solids mass flow rate of $m_{in}$ and with mass fractions of $x_{small}$ and $x_{large}$ for the smaller and larger diameter particles, respectively, typical cyclone design criteria will target the maximum possible efficiency, i.e., the solids flow rate exiting the bottom of the cyclone should approach the quantity of $(x_{small}+x_{large}) \cdot m_{in}$ as closely as possible. In the proposed application, the targeted solids flow rate exiting the bottom of the cyclone is $(x_{large}) \cdot m_{in}$, which allows a solids flow rate of $(x_{small}) \cdot m_{in}$ to exit from the top of the cyclone, effectively designing the cyclone for a lower efficiency to classify the particles. Specifically, the targeted efficiency will always be lower by the quantity equivalent to mass fraction of the smaller diameter particles in the solids feed (targeted efficiency of typical cyclone design=

$$\frac{(x_{small} + x_{large})m_{in}}{m_{in}},$$

targeted efficiency in this application $$\frac{(x_{large})m_{in}}{m_{in}}).$$

Figure 5:
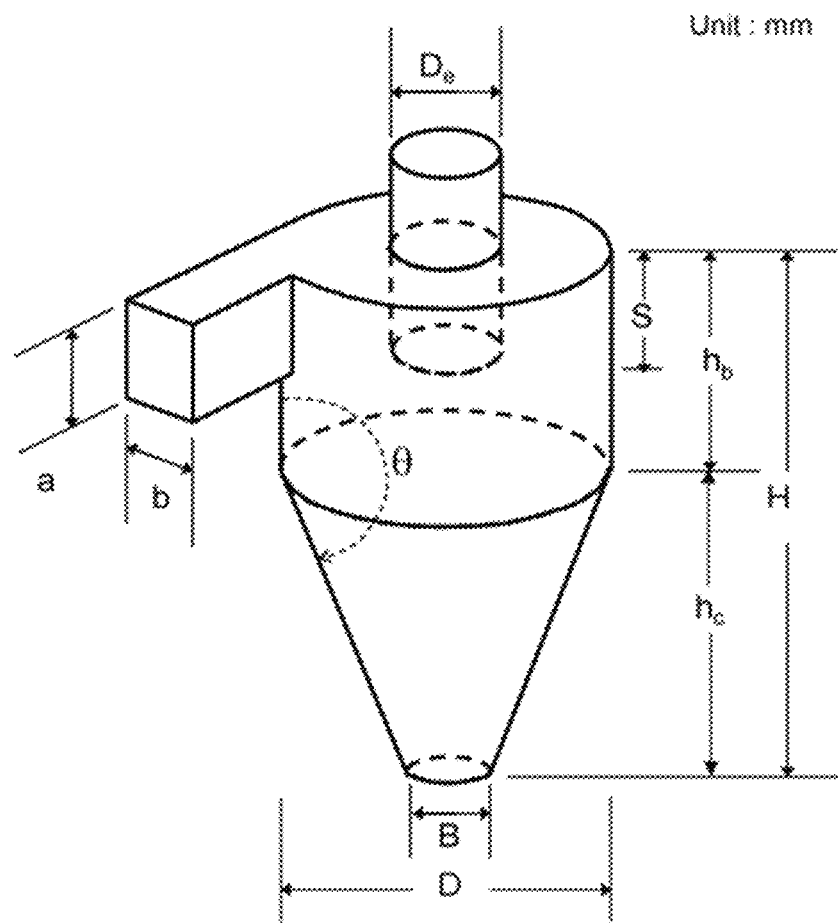
FIG. 5 shows the parameters that define the design of cyclones.

Therefore, the term low efficiency is used to describe the first stage cyclone. With reference to FIG. 5, or the product vapor solids separation system or the regenerator flue gas solids separation system, or both, within the classifier cyclone the ratio of vortex diameter ($D_e$) to cylinder diameter (D) can be 0.2, or 0.3, or 0.4, or 0.5, or 0.6, or 0.7, or lie within the range from 0.1 to 0.8, or from 0.3 to 0.7, or from 0.4 to 0.6, or from 0.45 to 0.55, or from 0.49 to 0.51. The ratio of vortex length (S) to cylinder length ($h_b$) can be 0.5, or 0.6, or 0.7, or 0.8, or 0.9, or lie within the range from 0.3 to 0.95, or from 0.5 to 0.95, or from 0.8 to 0.95, or from 0.85 to 0.95. The ratio of underflow diameter (B) to vortex diameter ($D_e$) can be 0.02, or 0.1, or 0.15, or 0.2, or 0.25, or 0.3, or 0.5, or 1.0, or 1.25, or lie within the range from 0.2 to 1.25, or from 0.02 to 0.5, or from 0.1 to 0.3, or from 0.15 to 0.25. The ratio of inlet height to inlet width can be 0.75, 1, or 1.5, or 2, or 2.4, or 3, or 4, or 5 or can lie within the range from 0.75 to 5, or from 1.5 to 4, or from 2 to 3, or from 2.2 to 2.6. The ratio of vortex length (S) to total height (H) can be 0.1, or 0.2, or 0.3, or 0.36, or 0.4, or 0.5, or 0.6, or 0.8, or lie within the range from 0.1 to 0.8, or from 0.2 to 0.6, or from 0.3 to 0.4, or from 0.34 to 0.38. The gas flow velocity at the entrance of the low efficiency or classifier cyclone is greater than 5, or greater than 10, or greater than 15, or from 5 to 40, or from 10 to 30, or from 15 to 25 meters/second.

Optionally, the catalyst that is removed from the catalytic reactor, or the catalyst that is recovered in the solids separation system, or both, can be stripped of volatile materials by passing a stream of steam, nitrogen, CO, $CO_2$, $CH_4$, He, or some combination of these, or a recycle stream from the product gases through the catalyst particles. The resulting vapor stream comprising steam and organic materials can be condensed, the organic and aqueous phases separated, and the liquid organic phase can be sent to product recovery and the aqueous phase can be sent to wastewater recovery. The catalyst that has been stripped of volatile organic compounds can be sent to the catalyst regenerator, or returned to the catalytic reactor, or discarded, or some combination thereof.

Figure 6:
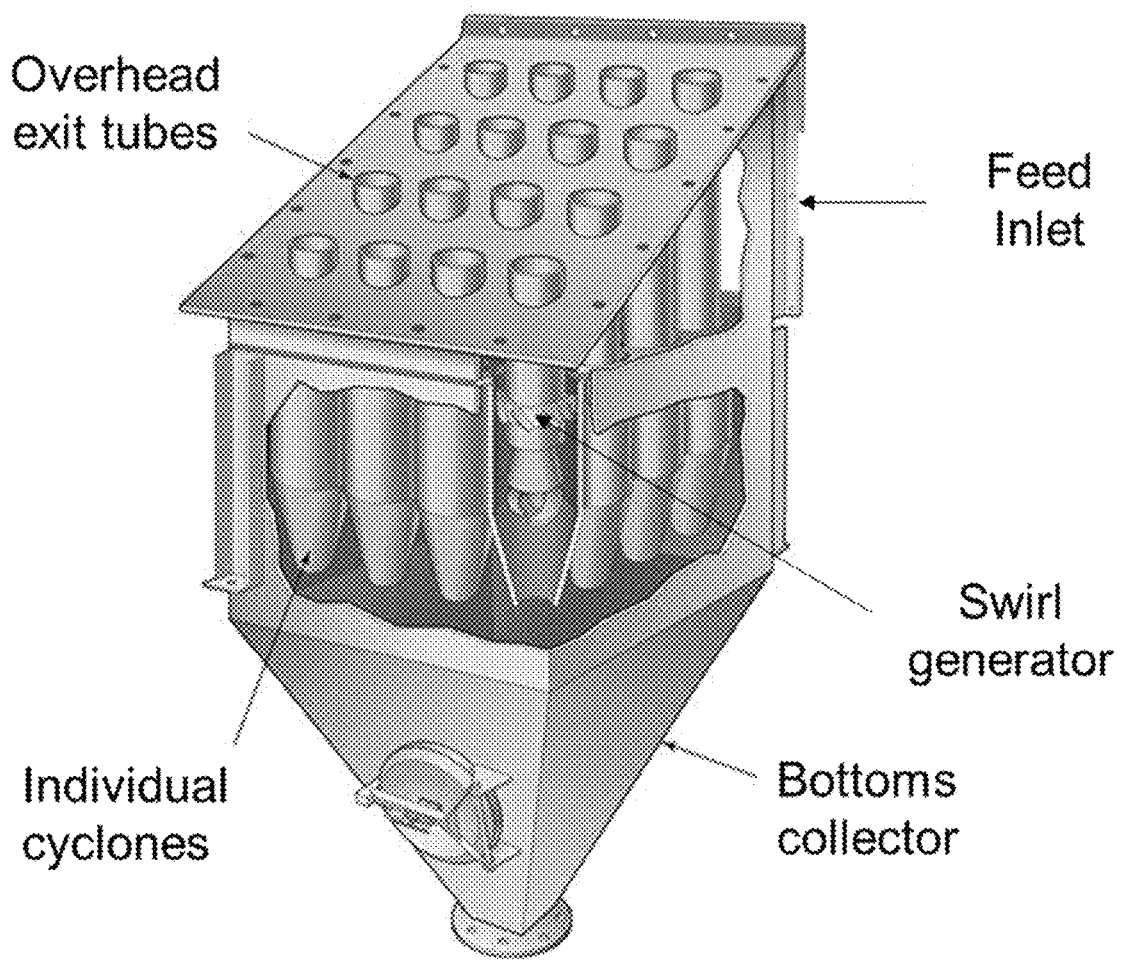
FIG. 6 shows the design of a multiclone.

The later stages of separation involve multiclones. Multiclones or multicyclones comprise multiple small-diameter tubes in parallel, each of which acts like a small cyclone. This configuration combines the high efficiency of a small diameter with the ability to treat large gas volumes. In each small diameter tube the gas flow rate is higher than in a larger diameter tube so that the efficiency of the separation is higher. The multiclone typically introduces a larger pressure drop than a comparable capacity single cyclone. FIG. 6 shows a schematic of a multiclone (https://www.babcock.com/home/products/multiclone-dust-collectors/) that can be used in the inventive process. Multiclones are used widely for reducing emissions levels on many biomass boilers and cement and lime kilns. They work by keeping the downstream equipment, like fractionators, fans, scrubbers, and precipitators working reliably with minimal energy input. They operate as a series of multiple high efficiency cyclones working in a parallel arrangement using a common inlet and outlet plenum. The process vapor stream enters the inlet plenum and is distributed to the many small, high efficiency, small diameter cyclones that can contain swirl generators. The different heights of the multiple smaller cyclones are designed to provide the same pressure drop and same flow rate through each. The particulates are released into a common solids exit plenum and the vapors exit from the device. These cyclones separate the majority of the particles from the gas stream as it flows through the system and can be used for particles as small as 5 microns in diameter.

With reference to FIG. 5, for each of the multiple small diameter cyclones within the multiclone, the ratio of vortex diameter ($D_e$) to cylinder diameter (D) can be 0.2, or 0.3, or 0.4, or 0.5, or 0.6, or 0.7, or lie within the range from 0.1 to 0.8, or from 0.3 to 0.7, or from 0.4 to 0.6, or from 0.45 to 0.55, or from 0.49 to 0.51. The ratio of vortex length (S) to cylinder length ($h_b$) can be 0.5, or 0.6, or 0.7, or 0.8, or 0.9, or lie within the range from 0.3 to 0.95, or from 0.5 to 0.95, or from 0.8 to 0.95, or from 0.85 to 0.95. The ratio of underflow diameter (B) to vortex diameter ($D_e$) can be 0.02, or 0.1, or 0.15, or 0.2, or 0.25, or 0.3, or 0.5, or 1.0, or 1.25, or lie within the range from 0.02 to 1.25, or from 0.02 to 0.5, or from 0.1 to 0.3, or from 0.15 to 0.25. The ratio of vortex length (S) to total height (H) can be 0.1, or 0.2, or 0.3, or 0.36, or 0.4, or 0.5, or 0.6, or 0.8, or lie within the range from 0.1 to 0.8, or from 0.2 to 0.6, or from 0.3 to 0.4, or from 0.34 to 0.38. The number of small cyclones within any one multiclone can be 4, 9, 16, 25, 36, 49, or 64, or from 4 to 64, or from 9 to 49, or from 16 to 36 cyclones. The gas flow velocity at the entrance of the recovery cyclones may be no more than 25, or no more than 20, or no more than 15, or from 3 to 20, or from 5 to 15, or from 6 to 12 meters/second.

In the separation of catalyst and fillers, at least a portion of the separated larger particle size entrained solids can be passed to the catalyst regenerator, or at least a portion can be returned to the catalytic pyrolysis reactor, or discarded, or some combination of these. The separated smaller particle solids can be passed to a separate regenerator, or to solid waste disposal. The product vapor stream from which the solids have been removed can contain no more than 150, or 300 or 500 mg of solids per $m^3$ of product vapors.

Optionally, the smaller solid particles that are recovered in the solids separation system can be stripped of volatile materials by passing a stream of steam, nitrogen, CO, $CO_2$, $CH_4$, He, or some combination of these, or a recycle stream from the product gases through the smaller solid particles. The resulting vapor steam comprising steam and organic materials can be condensed and the liquid organic phase can be sent to product recovery and the aqueous phase can be sent to wastewater recovery. The solid particles that have been stripped of volatile organic compounds can be sent to the filler regenerator, or discarded, or some combination thereof. In any of the methods, the step of catalytically pyrolyzing may comprise pyrolysis in the presence of a fluid bed catalyst. The catalytic pyrolysis reactor may comprise a fluidized bed, circulating bed, bubbling bed, turbulent bed or riser reactor operating at a temperature in the range from 300° C. to 800° C., or from 350° C. to 750° C., or from 400° C. to 700° C., or from 450° C. to 650° C., or from 500° C. to 600° C. The residence time of the vapors in the catalytic pyrolysis can be from 1 second to 480 seconds, or from 1 second to 240 seconds, or from 2 seconds to 60 seconds, or from 3 seconds to 30 seconds, or from 4 seconds to 15 seconds. The pressure of the catalytic pyrolysis reactor can be at least 0.1 MPa (1 bar), or at least 0.3 Mpa (3 bar), or at least 0.4 Mpa (4 bar), or from 0.1 to 2.0 Mpa (1 to 20 bar), or from 0.1 to 1.0 Mpa (1 to 10 bar), or from 0.3 to 0.8 Mpa (3 to 8 bar), preferably from 0.4 to 0.6 Mpa (4 to 6 bar), pressures are absolute pressures.

Design and conditions of the fluidized bed catalytic reactor can be those conventionally known. A fluidization gas may be needed at start-up; during steady-state operation, recycle gas from the process may be used as a component of the fluidizing gas. The fluidization gas can comprise $H_2$, CO, $CO_2$, $H_2O$, $C_1$-$C_4$ paraffins or olefins or both, $N_2$, Ar, He, or a recycle stream, or some combination thereof.

For catalytic pyrolysis, useful catalysts include those containing internal porosity selected according to pore size (e.g., mesoporous and pore sizes typically associated with zeolites), e.g., average pore sizes of less than 10 nm, less than 5 nm, less than 2 nm, less than 1 nm, less than 0.5 nm, or smaller. In some embodiments, catalysts with average pore sizes of from 0.5 to 10 nm may be used. In some embodiments, catalysts with average pore sizes of between 0.5 and 0.65 nm, or between 0.59 and 0.63 nm may be used. In some cases, catalysts with average pore sizes of between 0.7 and 0.8 nm, or between 0.72 and 0.78 nm may be used.

A catalyst composition particularly advantageous in the catalytic pyrolysis fluidized bed reactor of the present invention comprises a crystalline molecular sieve characterized by an SAR (silica to alumina, $SiO_2$:$Al_2O_3$ mass ratio) greater than 12, or from 12 to 240, and a CI (constraint index) from 1 to 12. Non-limiting examples of these crystalline molecular sieves are those having the structure of ZSM-5, ZSM-11, ZSM-12, ZSM-22, ZSM-23, ZSM-35, ZSM-48, ZSM-50, or combinations thereof. As an embodiment, the catalyst composition comprises a crystalline molecular sieve characterized by an SAR from greater than 12 to 240 and a CI from 5 to 10, such as, for example, molecular sieves having the structure of ZSM-5, ZSM-11, ZSM-22, ZSM-23 or combinations thereof. The method by which CI is determined is described more fully in U.S. Pat. No. 4,029,716, incorporated herein by reference for details of the method.

The molecular sieve for use herein or the catalyst composition comprising same may be thermally treated at high temperatures. This thermal treatment is generally performed by heating at a temperature of at least 370° C. for at least 1 minute and generally not longer than 20 hours (typically in an oxygen containing atmosphere, preferably air). While subatmospheric pressure can be employed for the thermal treatment, atmospheric pressure is desired for reasons of convenience. The thermal treatment can be performed at a temperature up to about 925° C. The thermally treated product is particularly useful in the present process.

For catalyst compositions useful in this invention, a suitable molecular sieve may be employed in combination with a support or binder material such as, for example, a porous inorganic oxide support or a clay binder. Non-limiting examples of such binder materials include alumina, zirconia, silica, magnesia, thoria, titania, boria, and combinations thereof, generally in the form of dried inorganic oxide gels and gelatinous precipitates. Suitable clay materials include, by way of example, bentonite, kieselguhr, and combinations thereof. The relative proportion of suitable crystalline molecular sieve of the total catalyst composition may vary widely with the molecular sieve content ranging from 30 to 90 percent by weight and more usually in the range of 40 to 70 percent by weight of the composition. The catalyst composition may be in the form of an extrudate, beads or fluidizable microspheres.

The molecular sieve or the catalyst composition comprising it may have original cations replaced, in accordance with techniques well known in the art, at least in part, by ion exchange with hydrogen, or hydrogen precursor cations, or non-noble metal ions of Group VIII of the Periodic Table, i.e., nickel, iron or cobalt, or zinc, or gallium, or combinations thereof.

In processes in which catalyst from the catalytic pyrolysis is regenerated, heat is generated by the oxidation of coke, char, and other materials in a catalyst regenerator for use in the process, or for conversion to electricity for export. In one set of embodiments, an oxidizing agent is fed to the regenerator via a stream 151 as shown in FIG. 1. The oxidizing agent may originate from any source including, for example, a tank of oxygen, atmospheric air, steam, among others. In the regenerator, the catalyst is re-activated by reacting the catalyst with the oxidizing agent and heat is generated. A solid mixture comprising deactivated catalyst may comprise residual carbon and/or coke as well as coke or char from the process, which may be removed via reaction with the oxidizing agent in the regenerator. A portion of the gaseous products from the catalytic pyrolysis process can be fed to the catalyst regenerator to be combusted with the solid materials. The gaseous products may be first separated into an olefin rich stream and an olefin poor stream and at least a portion of the olefin poor stream may be fed to the catalyst regenerator. The regenerator in FIG. 1 comprises a vent stream 152 which may include regeneration reaction products, residual oxidizing agent, etc.

In any of the methods, the vapors exiting the catalyst regenerator are passed through a solids separation system comprising a series of cyclones to separate entrained solids into larger particle size and smaller particle size fractions. The separated larger particle size entrained solids can be passed to the catalytic pyrolysis reactor, or discarded, or some combination of these. The separated smaller particle solids can be passed to a separate regenerator, or to solid waste disposal. The flue gas from the catalyst regenerator from which the solids have been removed can contain no more than 12, or 35, or 50, or 150 μg of solids per cubic meter of product vapors, averaged either over a 24-hour period or over a year.

Regenerator Separation System

The combustion product gas (flue gas) that is produced in either the catalyst regenerator or filler regenerator or both can be passed to a solids separation system similar to that described for the product vapor stream, either to separate solids separation systems, or as a combination of flue gases from both catalyst and filler regenerators sent to a common solids separation system. The solid separation system employed for removing particulates from the flue gas stream or streams can comprise a series of cyclones with an optional classifying cyclone followed by one or more high efficiency multiclones. The flue gas from the catalyst regenerator from which the solids have been removed can contain no more than 12, or 35, or 50, or 150 μmg of solids per cubic meter of product vapors, averaged either over a 24-hour period or over a year.

With reference to FIG. 5, for the flue gas solids separation system the dimensions of the classifier cyclone (optional) and the recovery cyclones (multiclones) can adhere to the same ratios of length as those described above for the product vapor purification solids separation system, although the absolute size of the cyclones may be different. The gas flow velocity at the entrance of the optional low efficiency or classifier cyclone is greater than 5, or greater than 10, or greater than 15, or from 5 to 40, or from 10 to 30, or from 15 to 25 meters/second. The gas flow velocity at the entrance of the high efficiency recovery cyclones is no more than 25, or no more than 20, or no more than 15, or from 7 to 20, or from 5 to 15, or from 6 to 12 meters/second.

In the inventive methods, at least a portion of the solid materials 123 can be removed from thermal treatment reactor 115 and may be recycled to the feed of thermal treatment reactor 115 as a portion of the optional co-reactant 122. The optional co-reactant 122 may comprise solid materials that react with sulfur or nitrogen compounds to trap the sulfur or nitrogen species in the solid phase. The solid materials in the optional co-reactant 122 can comprise one or more materials chosen from among agricultural lime, calcium oxide, calcium hydroxide, magnesium oxide, magnesium hydroxide, limestone, or hydrotalcites, activated carbon, or zeolite, or some combination thereof.

Multiple plastics upgrading units can be connected to feed a single product separation and purification facility in a hub and spoke system. A system for upgrading waste plastics comprises the optional first pyrolysis reactor and catalytic fluidized bed reactor that together form one spoke of a 'hub-and-spoke' network for producing refined chemical intermediates such as benzene, toluene, xylenes, p-xylene, m-xylene, o-xylene, BTX (a mixture of benzene, toluene, and xylenes), $C_6$-$C_{20}$ paraffins and olefins, ethylene, propylene, naphthalene, or others. or some combination of these, where each of the more than one plastics upgrading sites (the spokes) produces condensed phase products that are sent to a central processing facility (the hub) for separation and purification into product streams. The number of plastics upgrading facilities that can be in a network feeding a single central separation and purification facility can be at least 2, or at least 3, or at least 5, or at least 7, or at least 10, or at least 15, or from 2 to 20, or from 3 to 10, or from 5 to 10 plastics upgrading facilities. The total crude product mixture prepared at the plastics upgrading facilities that is introduced into a central separation and purification facility can be at least 20, or at least 50, or at least 100, or at least 150, or at least 200 metric tons per day, or from 20 to 500, or from 30 to 200, or from 50 to 150 metric tons per day of crude product mixture.

The invention also includes a system for upgrading plastics in which the plastics are first pyrolyzed in a pyrolysis reactor, each pyrolysis reactor may comprise one 'spoke' in a 'hub and spoke' network for producing refined chemical intermediates such as benzene, toluene, xylenes, p-xylene, m-xylene, o-xylene, BTX (a mixture of benzene, toluene, and xylenes), $C_6$-$C_{20}$ paraffins and olefins, ethylene, propylene, naphthalene, or others. or some combination of these, where each of the more than one plastics upgrading sites (the spokes) produces condensed phase products that are sent to a central processing facility (the hub) that includes a central fluidized bed catalytic process plant (Plas-TCat™) and separation and purification into product streams. In some embodiments of the system the number of plastics pyrolysis facilities that can be in a network feeding a single central catalytic upgrading, separation, and purification facility can be at least 2, or at least 3, or at least 5, or at least 7, or at least 10, or at least 15, or from 2 to 20, or from 3 to 10, or from 5 to 10 plastics pyrolysis facilities. The total crude product mixture prepared at the plastics pyrolysis facilities that is introduced into a central catalytic upgrading, separation, and purification facility can be at least 20, or at least 50, or at least 100, or at least 150, or at least 200 metric tons per day, or from 20 to 500, or from 30 to 200, or from 50 to 150 metric tons per day of crude product mixture.

EXAMPLES

Example 1

Figure 4:
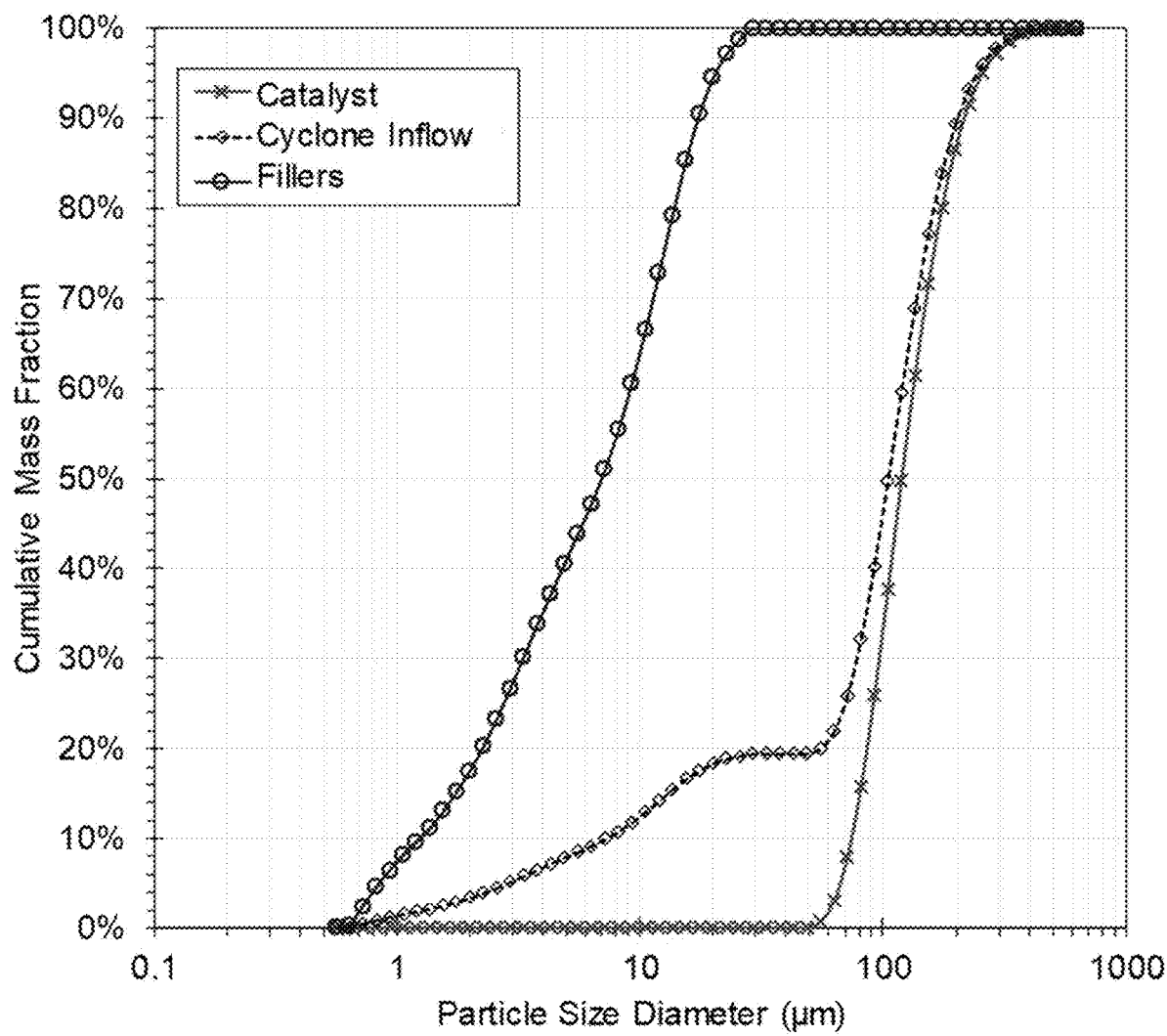
FIG. 4 presents the particle size distributions of the fillers, the catalyst, and the sum of the fillers and catalyst in the feed of Example 1.

A calculation was performed on the cyclones needed to separate and remove filler materials from the product effluent from the catalytic reactor in a system that processes 500 tonnes/day of mixed plastic containing 5% by weight of filler materials to produce useful products. The filler materials were assumed to have about 95% mass in particles less than 20 microns in size, and the catalyst was assumed to have 95% mass in particles larger than 65 microns in size. The particle size distributions of the fillers, the catalyst, and the sum of the fillers and catalyst ("cyclone inflow") in the feed are presented in FIG. 4. The plastic mixture is assumed to be catalytically pyrolyzed in a fluid bed catalytic reactor producing a product vapor stream of 5.2 kg/s with entrained solids including 1.2 kg/s of catalyst particles and 0.29 kg/s of filler particles. It was assumed that 10% of the feed mixture would produce coke deposited on the catalyst and material adsorbed in the interstitial pores of the catalyst that is sent to catalyst regeneration. Catalyst particles are assumed to have a density of 1300 kg/m$^3$ and the filler particles are assumed to have a density of 2700 kg/m$^3$. The gas density of the vapor stream is 1.65 kg/m3 at 500° C.

The solids separation system designed for the separation and removal of the solids includes 28 cyclones: one classifier, low efficiency cyclone, and three stages of purification multiclones that contain 9 internal cyclones in each stage. The dimensions of the cyclones and their performances are summarized in Table 3 for the parameters in FIG. 5 and FIG. 6. The masses of the materials that result from each of the cyclone stages for the solids separation system of Table 3 are summarized in Table 4. The fractions of each of the materials fed to each stage that are separated into the bottoms and overhead are summarized in Table 5. The destinations of the materials entering the catalytic reactor are presented in Table 6.

The calculations show that most of the catalyst is separated in the first, classifying cyclone, and the remainder comes out in Stage 2. The first cyclone was designed to target a lowered efficiency of 80.5%, which allows for complete removal of fillers that are 19.4% of the solids content in the inlet gas to the cyclone, an efficiency of 80.9% was calculated after optimizing the cyclone dimensions. Subsequently, the second, third and fourth separation stages were designed with a target overall efficiency of 99.6% which allows for the reduction of the fillers content in the gas down to the desired spec of 4 kg/hr, which corresponds to the solids limit that can enter downstream processing units. The majority of the desired separation (94.2%) was achieved in the second stage cyclone, whereas the third and fourth stages completed the separation to meet the target, the efficiencies of the third and fourth stage cycles were 77.4 and 74.4%, respectively, primarily due to the low required separation spec and the low content of solids in the entering gas to these stages, these efficiencies for the second, third and fourth were the highest possible achievable using the calculation approach used. The 3 stages of purification after the classification result in a gas stream that contains 4 kg/hr of filler particles that is suitable for introduction into a fractionator.

TABLE 3

Parameters for Cyclones in Example 1 for items in FIG. 5 and FIG. 6.

| Parameter | Symbol | Unit | Stage# 1 | Stage# 2 | Stage# 3 | Stage# 4 |
|---|---|---|---|---|---|---|
| Efficiency per stage | | % | 80.9 | 94.2 | 77.4 | 74.4 |
| Pressure drop | | kPa | 0.059 | 3.3 | 3.3 | 3.4 |
| Number of Cyclones in stage | | | 1 | 9 | 9 | 9 |
| Cylinder diameter | D | mm | 3000 | 250 | 250 | 250 |
| Vortex diameter | $D_e$ | mm | 1500 | 125 | 125 | 125 |
| Inlet width | b | mm | 750 | na | na | na |
| Cylinder length | $h_b$ | mm | 3000 | 250 | 250 | 250 |
| Vortex length | S | mm | 2700 | 225 | 225 | 225 |
| Total height | H | mm | 7500 | 625 | 625 | 625 |
| Underflow diameter | B | mm | 300 | 25 | 25 | 25 |
| Inlet Height | a | mm | 1800 | na | na | na |

TABLE 4

Flow rates of solids in the solids separation system of Example 1.

| | Inlet Stream | | Bottoms | | Overhead | |
|---|---|---|---|---|---|---|
| Stream | Catalyst kg/hr | Fillers kg/hr | Catalyst kg/hr | Fillers kg/hr | Catalyst kg/hr | Fillers kg/hr |
| Cyclone 1 | 4322 | 1042 | 4227 | 115 | 95 | 929 |
| Stage 2 | 95 | 929 | 95 | 867 | 0 | 62 |
| Stage 3 | 0 | 62 | 0 | 48 | 0 | 14 |
| Stage 4 | 0 | 14 | 0 | 14 | 0 | 4 |

TABLE 5

Fractions of feed materials found in each portion of the separated stream of Example 1.

| | Inlet Stream | | Bottoms | | Overhead | |
|---|---|---|---|---|---|---|
| Stream | Catalyst kg/hr | Fillers kg/hr | Catalyst % | Fillers % | Catalyst % | Fillers % |
| Cyclone 1 | 4322 | 1042 | 97.8% | 11.0% | 2.2% | 89.0% |
| Stage 2 | 95 | 929 | 100.0% | 93.3% | 0.0% | 6.7% |
| Stage 3 | 0 | 62 | na | 77.4% | na | 22.6% |
| Stage 4 | 0 | 14 | na | 71.4% | na | 28.6% |

TABLE 6

Destinations of the materials fed to the catalytic pyrolysis reactor.

| | Catalyst, kg/hr | Fillers, kg/hr | Catalyst | Fillers |
|---|---|---|---|---|
| Material returned to reactor | 4227 | 115 | 97.8% | 11.0% |
| Removed from process | 95 | 923 | 2.2% | 88.6% |
| Sent to fractionation | 0 | 4 | 0.0% | 0.4% |

Example 2

Figure 7:
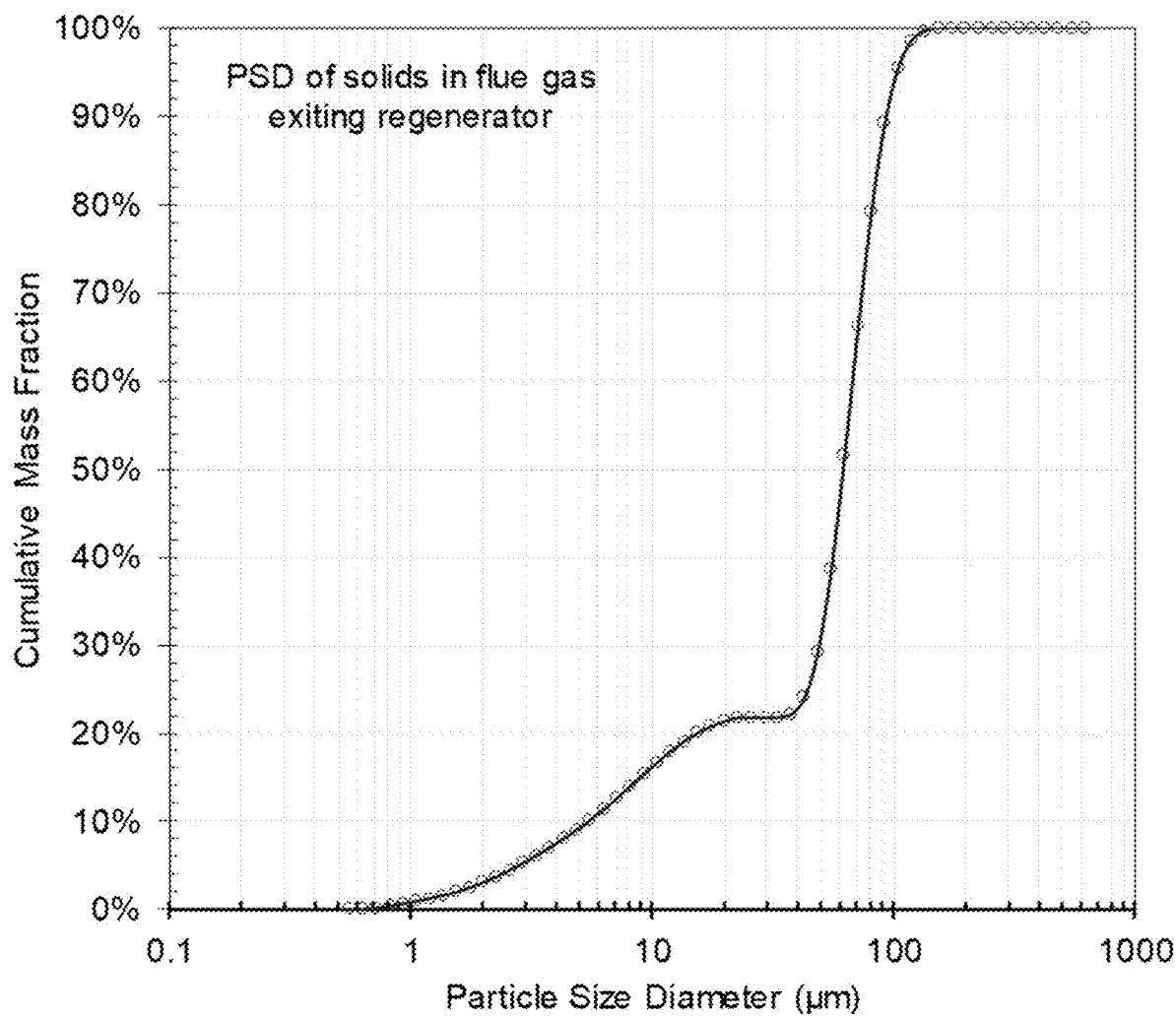
FIG. 7 shows the particle size distribution of the solids that exit the regenerator and that include fillers and catalyst that was determined experimentally.

A calculation was performed on the cyclones needed to separate and remove filler materials from the flue gas effluent from the catalyst regenerator in a plastics chemical recycling system that processes 500 metric tons/day of mixed plastic containing 5% by weight of filler materials to produce useful products. The filler materials were assumed to have about 95% mass in particles less than 20 microns in size, and the catalyst was assumed to have 95% mass in particles larger than 65 microns in size. The particle size distribution of the solids that exit the regenerator and that include fillers and catalyst that was determined experimentally is presented in FIG. 7. The solids to be separated include catalyst particles that have a density of 1300 kg/m$^3$ and filler particles that have a density of 2700 kg/m$^3$. The flow rate of the solids is 105 kg/s and the gas flow rate is 10.14 g/s. The gas density of the vapor stream is 1.8 kg/m3 at 500° C.

The solids separation system designed for the separation and removal of the solids includes 76 cyclones: one classifier, low efficiency cyclone, and three stages of multicyclones in series that contain 25 internal cyclones in each stage. The dimensions of the cyclones and their performances are summarized in Table 7 for the items in FIG. 5 and FIG. 6. The masses of the materials that result from each of the cyclone stages for the solids separation system of Table 5 are summarized in Table 8. The fractions of each of the materials fed to each stage that are separated into the bottoms and overhead are summarized in Table 9. The destinations of the materials entering the catalyst regenerator are presented in Table 10.

The calculations show that all of the catalyst is separated in the first, classifying cyclone. The first cyclone was designed to target a lowered efficiency of 99.7%, which allows for complete removal of fillers that are 19.4% of the solids content in the inlet gas to the cyclone. The first stage cyclone shows complete classification of the filler from the catalyst, with all the catalyst being recovered from the bottom of the cyclone and 97.25% of the filler being passed along with the gas phase. The second, third and fourth separation stages were designed with a target overall efficiency of 99.6% which allows for the reduction of the fillers content in the gas down to the desired spec of 4 kg/hr, which corresponds to the solids limit that can enter downstream processing units. The majority of the desired separation (94.8%) was achieved in the second stage cyclone, whereas the third and fourth stages completed the separation to meet the target, the efficiencies of the third and fourth stage cycles were 76.5 and 69.7%, respectively, primarily due to the low required separation spec and the low content of solids in the entering gas to these stages, these efficiencies for the second, third and fourth were the highest possible achievable using the calculation approach used. The 3 stages of purification, each with a multicyclone containing 25 cyclones, after the classification cyclone result in a flue gas stream that contains 3 kg/hr of filler particles that is allowable for emission into the air.

TABLE 7

Parameters for Cyclones in Example 2 for items in FIG. 5 and FIG. 6.

| Parameter | Symbol | Unit | Stage# 1 | Stage# 2 | Stage# 3 | Stage# 4 |
|---|---|---|---|---|---|---|
| Efficiency per stage | | % | 99.7 | 94.8 | 76.5 | 69.7 |
| Pressure drop | | kPa | 6.1 | 3.1 | 3.2 | 3.3 |
| Number of Cyclones per stage | | | 1 | 25 | 25 | 25 |
| Cylinder diameter | D | mm | 1350 | 250 | 250 | 250 |
| Vortex diameter | $D_e$ | mm | 675 | 125 | 125 | 125 |
| Inlet width | b | mm | 337 | na | na | na |
| Cylinder length | $h_b$ | mm | 1350 | 250 | 250 | 250 |
| Vortex length | S | mm | 1215 | 225 | 225 | 225 |
| Total height | H | mm | 3375 | 625 | 625 | 625 |
| Underflow diameter | B | mm | 135 | 25 | 25 | 25 |
| Inlet Height | a | mm | 810 | na | na | na |

TABLE 8

Mass flows of solids in the solids separation system of the catalyst regenerator in Example 2.

| Stream | Inlet Stream | | Bottoms | | Overhead | |
|---|---|---|---|---|---|---|
| | Catalyst kg/hr | Fillers kg/hr | Catalyst kg/hr | Fillers kg/hr | Catalyst kg/hr | Fillers kg/hr |
| Cyclone 1 | 377,000 | 1055 | 377,000 | 29 | 0 | 1026 |
| Stage 2 | 0 | 1026 | 0 | 973 | 0 | 53 |
| Stage 3 | 0 | 53 | 0 | 41 | 0 | 13 |
| Stage 4 | 0 | 13 | 0 | 10 | 0 | 3 |

TABLE 9

Fractions of feed materials found in each portion of the separated stream in Example 2.

| | Inlet Stream | | Bottoms | | Overhead | |
|---|---|---|---|---|---|---|
| Stream | Catalyst, kg/hr | Fillers, kg/hr | Catalyst | Fillers | Catalyst | Fillers |
| Cyclone 1 | 377000 | 1055 | 100.0% | 2.7% | 0.0% | 97.3% |
| Stage 2 | 0 | 1026 | na | 94.8% | na | 5.2% |
| Stage 3 | 0 | 53 | na | 77.4% | na | 24.5% |
| Stage 4 | 0 | 13 | na | 76.9% | na | 23.1% |

TABLE 10

Destinations of feed materials in Example 2.

| | Catalyst, kg/hr | Fillers, kg/hr | Catalyst | Fillers |
|---|---|---|---|---|
| Material returned to reactor | 377000 | 29 | 100.0% | 2.7% |
| Removed from process | 0 | 1023 | 0.0% | 97.0% |
| Emitted in flue gas | 0 | 3 | 0.0% | 0.3% |

Example 3

A small pilot plant for upgrading waste plastic or other materials was constructed with a bubbling fluid bed of catalyst, a stripper to remove and recover materials deposited on the catalyst, a regenerator to regenerate the catalyst, and a solids separation system to separate catalyst from fillers. The process parameters are shown in Table 11.

TABLE 11

Process parameters for Example 3.

| Parameter | Value |
|---|---|
| Bed Height (m) | 1.7 |
| Catalyst circulation rate (kg/hr) | 180 |
| Fluidization Gas Velocity (m/s) | 0.18 |
| Average Plastic Feeding Rate (kg/hr) | 8.3 |
| WHSV (gfeed/gcath) | 0.193 |
| Reactor Temperature (° C.) | 550 |
| Reactor Pressure (barg) | 4 |
| Cyclone #1 Temperature (° C.) | 438 |

Figure 8:
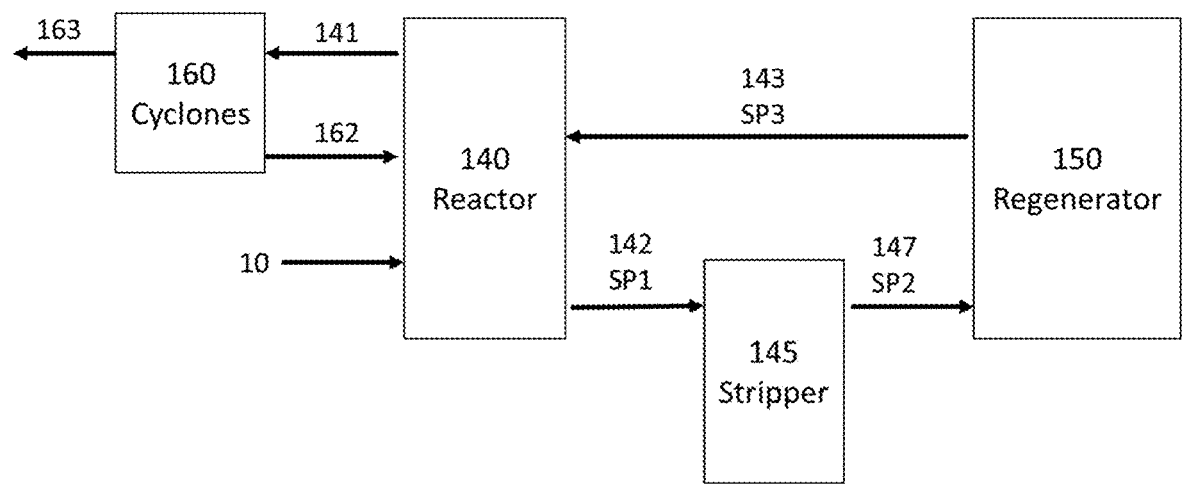
FIG. 8 shows a schematic of a pilot plant reactor that was operated with a solids separation system.

A schematic of the flow of solids within the pilot plant is presented in FIG. 8, comprising the fluid bed reactor 140, a stripper 145, a catalyst regenerator 150, and a solids separation system 160. Plastic 10 was fed to the catalytic fluid bed reactor, catalyst 142 was continuously withdrawn and stripped with N2 to produce a stripped catalyst 147 which was regenerated in the regenerator 150, and the regenerated catalyst 143 returned to the reactor. The fluid product stream 141 was passed to a solids separation system 160 that included 2 solid separation cyclones in series with larger particles from both cyclones returned to the reactor and the vapor stream from the first cyclone passed to the second cyclone. The cyclones separated larger particles (mostly catalyst) 162 from the smaller particles in the vapor product stream 163; the larger particles were returned to the catalytic fluid bed reactor. The dimensions of the cyclones of the design in FIG. 5 are summarized in Table 12.

TABLE 12

Dimensions of cyclones used in Example 3.

| Name | Label | Value |
|---|---|---|
| Cylinder diameter | D | 4.026 inch, 10.2 cm |
| Vortex diameter | $D_e$ | 1.38 in, 3.5 cm |
| Inlet width | b | 2.5", 6.35 cm |
| Cylinder length | $h_b$ | 4", 10.16 cm |
| Vortex length | S | 1.75", 4.445 cm |
| Total height | H | 16.5", 41.91 cm |
| Underflow diameter | B | 1.38 in, 3.5 cm |
| Inlet Height | a | 2 ⅛ in, 5.3975 cm |

TABLE 13

Cyclone characterization parameters for cyclones of Example 3.

| Parameter | Value |
|---|---|
| De/D | 0.343 |
| $S/h_b$ | 0.4375 |
| $B/D_e$ | 1 |
| a/b | 0.85 |
| S/H | 0.11 |

The catalytic reactor was charged with catalyst, the plant was brought to operating conditions by heating the reactor and regenerator and the flows were established with inert gas (N2). The reactor was allowed to come to a steady state by operation without feed for 24 hours. A feed of plastic was initiated after 24 hours on stream and the reactor was operated for 5.5 hours with plastic feed containing fillers. Samples were taken after 3.5 hours of plastic feed. After the 5.5 hours of plastic feed, the reactor was operated for 42 hours without any feed but kept hot in a holding condition.

The feed of plastic-containing fillers was re-initiated at the 71.5 TOS mark and continued for 5.5 hours. Samples were withdrawn at the 75.5 TOS mark, at which point the system had been fed plastic for a total of 9.5 hours.

Several PSD samples were taken at various locations in the process. The sample SP1 (standpipe 1) was taken from the standpipe between the reactor and the stripper, SP2 was taken from the standpipe between the stripper and the regenerator, and SP3 was taken from the standpipe between the regenerator and the reactor as shown in FIG. 8.

The particle size distribution (PSD) was determined using a Mastersizer 3000 (Manufacturer Malvern Panalytical) by dispersing the material into deionized water and measured for particle size (volume density).

Figure 9:
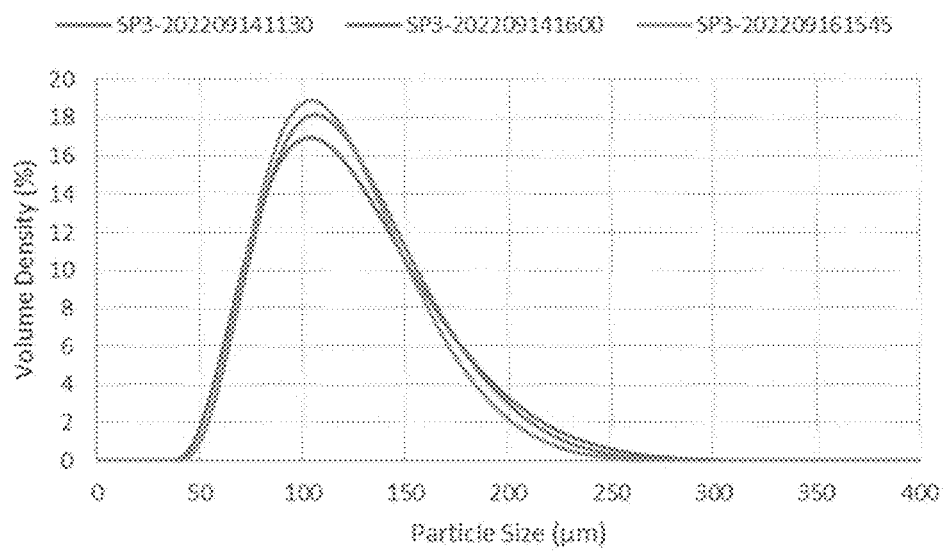
FIG. 9 shows particle size distributions (PSDs) measured for the regenerated catalyst from standpipe 3. PSDs measured for the regenerated catalyst from standpipe 3 after 24 hrs TOS before introducing filler containing plastic feed (lowest peak), at 27.5 hrs TOS after 3.5 hours of plastic feeding at a rate of 6.5 kg/hr (middle size peak), at 75.5 hours TOS after 9.5 hours of plastic feeding at a rate of 6.5 kg/hr (highest peak).

In FIG. 9 the PSDs of regenerated catalyst samples were determined to be unimodal with similar distributions at 24, 27.5, and 75.5 hours on stream. The maximum volume density was measured at particle size of 105-110 μm. At an early time-on-stream (24 hrs TOS) the PSD is broader. As TOS progresses, the distribution narrows the as the larger particles are attrited and smaller particles are entrained and removed from the product vapors by the 2 cyclones in the solids separation system.

Figure 10:
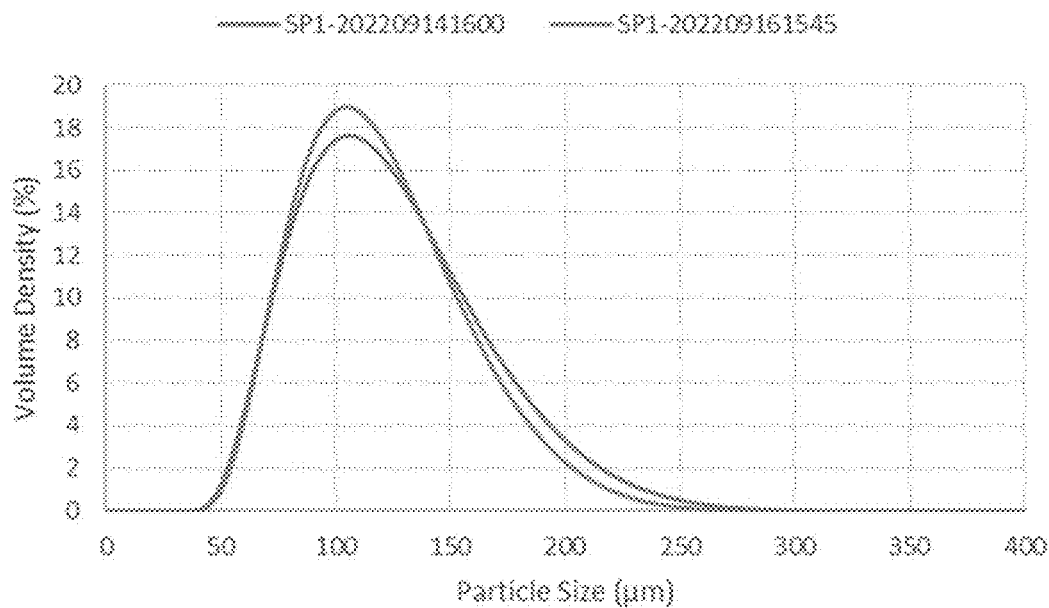
FIG. 10 shows the particle size distribution (PSD) of unstripped reactor catalyst from standpipe 1 at 27.5 hrs TOS after 3.5 hours of plastic feeding at a rate of 6.5 kg/hr (lower peak), at 75.5 hours TOS after 9.5 hours of plastic feeding at a rate of 6.5 kg/hr (taller peak).
Figure 11:
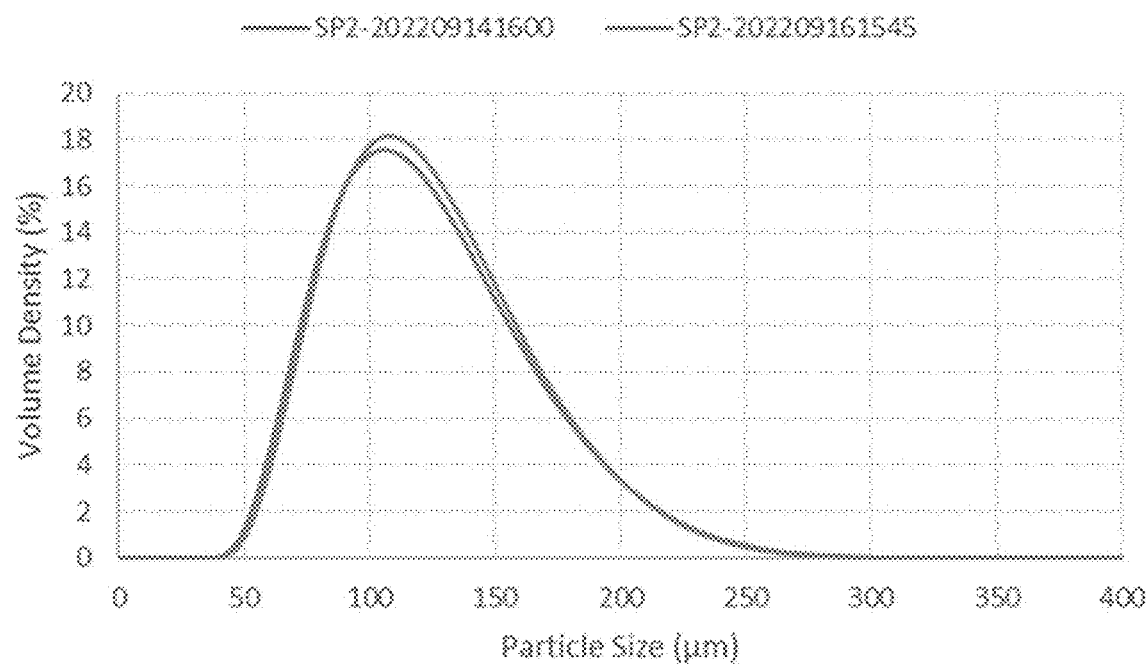
FIG. 11 shows the PSD of stripped reactor catalyst at 27.5 hrs TOS after 3.5 hours of plastic feeding at a rate of 6.5 kg/hr (shorter peak), at 75.5 hours TOS after 9.5 hours of plastic feeding at a rate of 6.5 kg/hr (taller peak).

FIG. 10 shows that the PSD profiles of the unstripped catalyst in standpipe 1 are unimodal and the maximum volume density was measured at particle size of 105-110 m at all times on stream. As before, the PSD at an earlier TOS is broader and, as TOS increases, the distribution becomes slightly narrower. Similarly, FIG. 11 shows the PSD profiles of the stripped catalyst for the 3 different times on stream, and the earlier time is a broader distribution than the later TOS.

Figure 12:
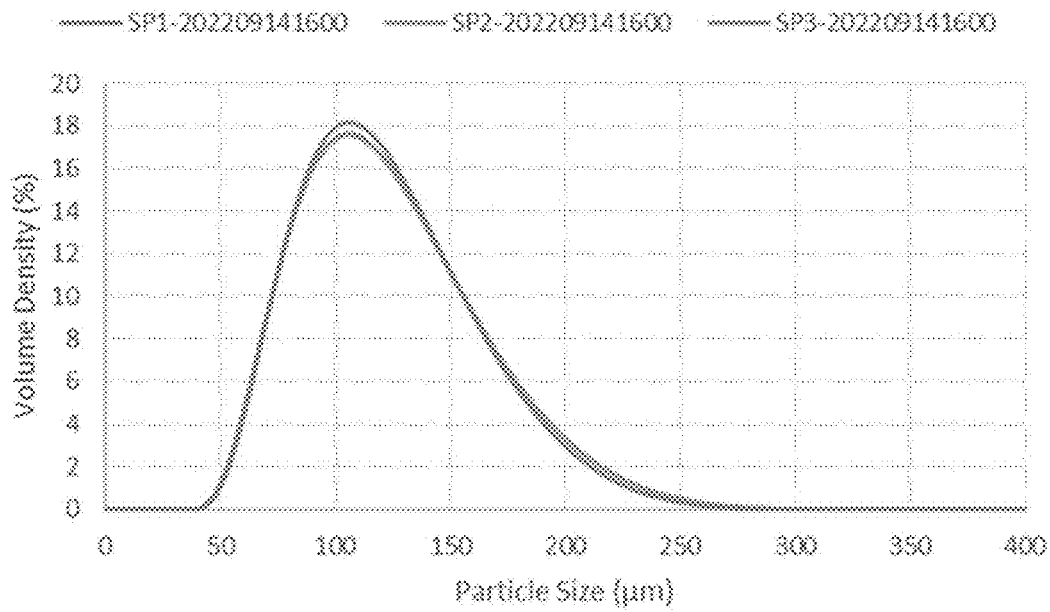
FIG. 12 shows PSDs of samples from standpipes 1 (unstripped), 2 (stripped), and 3 (regenerated) at 27.5 hrs TOS after 3.5 hours of plastic feeding at a rate of 6.5 kg/hr. The taller peak is from the regenerated catalyst while the shorter peak shows the other two PSDs that overlay each other.

FIG. 12, presents PSDs of samples from standpipes 1 (unstripped), 2 (stripped), and 3 (regenerated) at 27.5 hrs TOS after 3.5 hours of plastic feeding at a rate of 6.5 kg/hr, The taller peak is from the regenerated catalyst while the shorter peak shows the other two PSDs that overlay each other. It is believed that the slightly broader PSDs may be due to coke that builds up to a few percent by weight on the catalyst and is burnt off in the regenerator.

Figure 13:
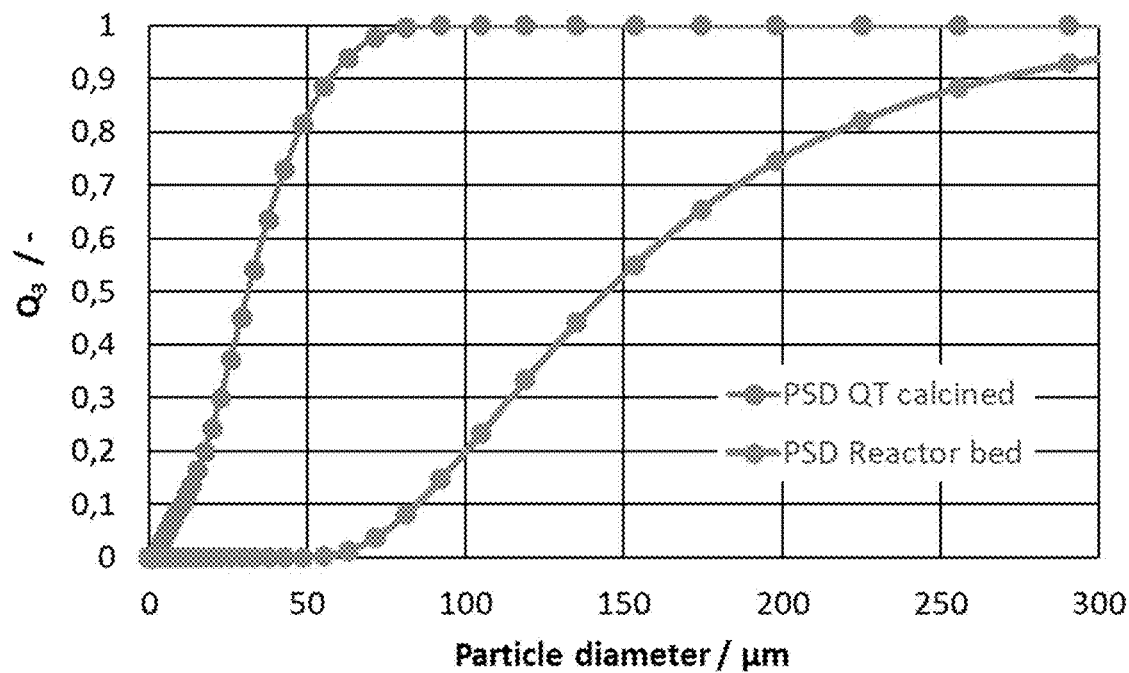
FIG. 13 shows a comparison of the PSD of the material that passes through the solids separation system (upper data) to the PSD of the catalyst in the fluid bed (lower data). Each data point represents the mass fraction of that sample that comprises particles smaller than a particular diameter.

In order to understand the classification of the separation system, a sample of the solids trapped in a quench downstream of the solids separation system was calcined and evaluated. The PSD of the ash was measured and presented along with the PSD of the catalyst in the fluid bed in FIG. 13. The ash that was separated in the solids separation system has about 80% by mass of particles smaller than 50 microns whereas the catalyst bed has less than 1% by mass of particles smaller than 50 microns. This shows that the two cyclones are able to classify the particles by particle size into those smaller than 80 microns and those larger than 80 microns with high efficiency.

Example 4

A calculation was performed using Computational Particle Fluid Dynamics (CPFD) modeling on the cyclones needed to separate and remove filler materials from the product effluent from the catalytic reactor in a system that processes 500 tonnes/day of mixed plastic containing 5% by weight of filler materials into useful products. The filler materials were assumed to have about 95% mass in particles less than 20 microns in size, and the catalyst was assumed to have 95% mass in particles larger than 65 microns in size. The particle size distributions of the fillers, the catalyst, and the sum of the fillers and catalyst ("cyclone inflow") in the feed are presented in FIG. 4. The plastic mixture is assumed to be catalytically pyrolyzed in a fluid bed catalytic reactor producing a product vapor stream of 5.2 kg/s with entrained solids including 1.2 kg/s of catalyst particles and 0.29 kg/s of filler particles. It was assumed that 10% of the feed mixture is deposited on the catalyst as either coke or material adsorbed in the interstitial pores of the catalyst. Catalyst particles are assumed to have a density of 1300 kg/m3 and the filler particles are assumed to have a density of 2700 kg/m3. The gas density of the vapor stream is 1.65 kg/m3 at 500° C.

The CPFD model included the primary classification (low efficiency) cyclone, which is designed for the separation of the filler from the catalyst material. The dimensions of the cyclone are summarized in Table 14. Simulations were carried out over a range of conditions for the reactor inlet fluidization velocity and amount of fillers entering the reactor and the results are summarized in Table 15. In all cases, the proposed classifier design was able to remove fillers from the product vapors, with the fraction of fillers removed ranging from 72-910 while essentially 10000 of the catalyst is recovered to be returned to the reactor.

This example shows that a classifier cyclone can efficiently separate fillers from the product vapors without loss of catalyst for recycle to the reactor.

TABLE 14

Parameters for CFD Evaluation of Classifying Cyclone.

| Parameter | Symbol | Unit | Dimension |
|---|---|---|---|
| Number of Cyclones per stage | | | 1 |
| Cylinder diameter | D | mm | 1350 |
| Vortex diameter | $D_e$ | mm | 675 |
| Inlet width | b | mm | 337 |
| Cylinder length | $h_b$ | mm | 1350 |
| Vortex length | S | mm | 1215 |
| Total height | H | mm | 3375 |
| Underflow diameter | B | mm | 135 |
| Inlet Height | a | mm | 810 |

TABLE 15

Results of CFD Evaluation of Cyclone Performance.

| Case # | Reactor Inlet Fluidization Velocity (m/sec) | % Filler in Feed | Cyclone inlet velocity (m/s) | Pressure Drop (kPa) | Catalyst Removal Efficiency (%) | % Filler Removed From Stream |
|---|---|---|---|---|---|---|
| 1 | 0.05 | 5 | 13.41 | 0.92 | 100 | 91 |
| 2 | 0.10 | 5 | 15.27 | 1.19 | 100 | 88 |
| 3 (Base Case) | 0.15 | 5 | 17.14 | 1.52 | 100 | 85 |
| 4 | 0.20 | 5 | 19.00 | 1.85 | 100 | 82 |
| 5 | 0.30 | 5 | 22.73 | 2.65 | 100 | 77 |
| 6 | 0.40 | 5 | 26.46 | 3.58 | 100 | 72 |
| 7 | 0.15 | 1 | 13.41 | 1.49 | 100 | 85 |
| 8 | 0.15 | 2 | 13.41 | 1.49 | 100 | 85 |
| 9 | 0.15 | 3 | 13.41 | 1.49 | 100 | 85 |
| 10 | 0.15 | 4 | 13.41 | 1.49 | 100 | 85 |
| 11 | 0.15 | 10 | 13.41 | 1.49 | 100 | 85 |

What is claimed:

1. A method for producing olefins and aromatics comprising:

passing a feed stream comprising plastics, at least one of which contains filler material, to a fluidized bed reactor comprising a catalyst; wherein the filler material has a particle size that is smaller than a particle size of the fluid bed catalyst;

catalytically reacting the feed stream with the catalyst in the fluidized bed reactor to form a product mixture comprising a first mass ratio of catalyst to filler material;

recovering a vapor effluent from the product mixture, wherein the vapor effluent comprises catalyst particles and filler material;

passing the vapor effluent through a solids separation system comprising passing the vapor effluent into a first cyclone and separating a first bottoms fraction and a first overflow fraction;

wherein the first cyclone is a classifier cyclone;

wherein the first bottoms fraction has a second mass ratio that is greater than the first mass ratio;

passing the overflow fraction from the first cyclone into a second cyclone and separating a second bottoms fraction and a second overflow fraction;

wherein the first cyclone has a first separation efficiency for the catalyst particles and the second cyclone has a second separation efficiency for the particles that is greater than the first separation efficiency;

wherein the second bottoms fraction has a third mass ratio that is less than the first mass ratio;

discarding the second bottoms fraction and recovering olefins, aromatics, or some combination thereof from the second overflow fraction exiting the second cyclone.

2. The method of claim 1 wherein the second cyclone or series of cyclones comprises one or more recovery cyclones or multiclones.

3. The method of claim 1 wherein at least a portion of solids recovered in the first bottoms fraction from the one or more classifier cyclones is returned to the fluidized bed reactor.

4. The method of claim 1 wherein a stream comprising more ethylene, propylene, or both than the feed stream is separated from volatile products.

5. The method of claim 1 wherein the catalyst is a solid catalyst and wherein the step of catalytically reacting is catalytically pyrolyzing and comprises pyrolyzing in the presence of the solid catalyst in the fluidized bed reactor to produce the vapor effluent and used catalyst with coke, and wherein at least 90% of the carbon in the feed is converted to coke and volatile products.

6. The method of claim 1 wherein the feed stream comprises the plastics chosen from among polyethylene, polypropylene, polyesters, polyethylene terephthalate (PET), acrylonitrilebutadiene-styrene (ABS) copolymers, polyethylenefuranoate (PEF), polyamide, polyurethane, polyethers, polycarbonates, poly(oxides), poly(sulfides), polyarylates, polyetherketones, polyetherimides, polysulfones, polyurethanes, polyvinyl alcohols; polymers produced by polymerization of monomers comprising dienes, olefins, styrenes, acrylates, acrylonitrile, methacrylates, methacrylonitrile, diacids and diols, lactones, diacids and diamines, lactams, vinyl esters, block copolymers thereof, and alloys thereof; thermoset polymers comprising epoxy resins phenolic resins, melamine resins, alkyd resins, vinyl ester resins unsaturated polyester resins, crosslinked polyurethanes, and polyisocyanurates; crosslinked elastomers comprising polyisoprene, polybutadiene, styrene-butadiene, styrene-isoprene, and ethylene-propylene-diene monomer polymer; and mixtures thereof.

7. The method of claim 1 wherein the catalyst in the fluidized bed reactor comprises a zeolite.

8. The method of claim 1 wherein a solid co-reactant comprising agricultural lime, calcium oxide, calcium hydroxide, magnesium oxide, magnesium hydroxide, limestone, hydrotalcites, activated carbon, zeolite, other solid basic material, or some combination thereof, is fed to a thermal treatment reactor.

9. The method of claim 1 wherein the vapor effluent from the fluidized bed catalytic reactor comprises at least 10 mass % BTX, or in a range of 10 to 90 mass % BTX.

10. The method of claim 1 wherein the vapor effluent comprises CH4 and C2-C4 paraffins; and wherein 50 to 100 mass % of the CH4 and C2-C4 paraffins is combusted in a regenerator.

11. The method of claim 1 wherein, in one or more of the classifier cyclones, a ratio of vortex diameter to cylinder diameter can be 0.2, or 0.3, or 0.4, or 0.5, or 0.6, or 0.7, or lie within a range from 0.1 to 0.8, or from 0.3 to 0.7, or from 0.4 to 0.6, or from 0.45 to 0.55, or from 0.49 to 0.51, or a ratio of vortex length (S) to cylinder length can be 0.5, or 0.6, or 0.7, or 0.8, or 0.9, or lie within a range from 0.3 to 0.95, or from 0.5 to 0.95, or from 0.8 to 0.95, or from 0.85 to 0.95, or a ratio of underflow diameter to the vortex diameter can be 0.02, or 0.1, or 0.15, or 0.2, or 0.25, or 0.3, or 0.5, or 1.0, or 1.25, or lie within a range from 0.02 to 1.25, or from 0.02 to 0.5, or from 0.1 to 0.3, or from 0.15 to 0.25, or a ratio of inlet height to inlet width can be 0.75, or 1, or 1.5, or 2, or 2.4, or 3, or 4, or 5 or can lie within a range from 0.75 to 5, or from 1.5 to 4, or from 2 to 3, or from 2.2 to 2.6, or a ratio of the vortex length (S) to total height (H) can be 0.1, or 0.2, or 0.3, or 0.36, or 0.4, or 0.5, or 0.6, or 0.8, or lie within a range from 0.1 to 0.8, or from 0.2 to 0.6, or from 0.3 to 0.4, or from 0.34 to 0.38.

12. The method of claim 2 wherein the one or more recovery cyclones comprises at least one multiclone.

13. The method of claim 1 wherein the feed stream is treated in a thermal treatment reactor and condensed phases are passed to the fluidized bed reactor.

14. The method of claim 8 wherein at least a portion of the solid co-reactant material is separated from the product stream of the thermal treatment reactor and transferred to a combustion regenerator, wherein the carbonaceous materials are reacted with air and at least a portion of a hot solid co-reactant material is returned to the thermal treatment reactor.

15. The method of claim 14 wherein a hot flue gas exiting the combustion regenerator is passed to a catalyst heater to heat the catalyst for the fluidized bed reactor.

16. The method of claim 2 wherein filler material is recovered from the solids separation system.

17. The method of claim 16 wherein the filler material that is recovered in the solids separation system stripped of volatile materials by passing a stream of steam, nitrogen, CO, $CO_2$, $CH_4$, He, or some combination of these, or a recycle stream from the product gases through the filler material, condensing the stream, separating organic and aqueous phases, sending the organic phase to product recovery, sending the aqueous phase to wastewater recovery, and sending the filler material that has been stripped of volatile materials to the filler regenerator, discarding the filler material, or a combination thereof.

18. The method of claim 1 wherein the mass ratio of catalyst particles to filler particles entering the classifier cyclone is at least 1, 2, 5, 10, 20, 30, or 50, or from 0.1 to 50, from 0.5 to 30, or from 5 to 20.

* * * * *